United States Patent
Erickson et al.

(10) Patent No.: US 7,924,424 B2
(45) Date of Patent: Apr. 12, 2011

(54) OPTICAL PRODUCT DETECTION SENSOR

(75) Inventors: Joseph Erickson, Cloquet, MN (US); Eugene Tokhtuev, Duluth, MN (US); Christopher Owen, Duluth, MN (US)

(73) Assignee: Ecolab USA Inc., Saint Paul, MN (US)

( * ) Notice: Subject to any disclaimer, the term of this patent is extended or adjusted under 35 U.S.C. 154(b) by 149 days.

(21) Appl. No.: 12/428,738

(22) Filed: Apr. 23, 2009

(65) Prior Publication Data

US 2009/0262351 A1    Oct. 22, 2009

Related U.S. Application Data

(63) Continuation-in-part of application No. 12/247,743, filed on Oct. 8, 2008.

(51) Int. Cl.
*G01N 21/00* (2006.01)
(52) U.S. Cl. ..................................... 356/432
(58) Field of Classification Search ........... None
See application file for complete search history.

(56) References Cited

U.S. PATENT DOCUMENTS

| | | |
|---|---|---|
| 3,935,876 A | 2/1976 | Massie et al. |
| 4,105,334 A | 8/1978 | Halko et al. |
| 4,114,144 A | 9/1978 | Hyman |
| 4,312,341 A | 1/1982 | Zissimopoulos et al. |
| 4,344,429 A | 8/1982 | Gupton et al. |
| 4,366,384 A | 12/1982 | Jensen |
| 4,622,465 A | 11/1986 | Harig |
| 4,658,244 A | 4/1987 | Meijer |
| 4,700,870 A | 10/1987 | Schleicher et al. |
| 4,764,166 A | 8/1988 | Spani |
| 4,784,643 A | 11/1988 | Siretchi et al. |
| 4,829,448 A | 5/1989 | Balding et al. |
| 4,857,050 A | 8/1989 | Lentz et al. |
| 5,006,110 A | 4/1991 | Garrison et al. |
| 5,083,862 A | 1/1992 | Rusnak |
| 5,102,392 A | 4/1992 | Sakai et al. |

(Continued)

FOREIGN PATENT DOCUMENTS

EP        1533597        5/2005

(Continued)

OTHER PUBLICATIONS

International Search and the Written Opinion, dated Aug. 26, 2009 for corresponding PCT Application No. PCT/IB2008/054134 (6 pages).

(Continued)

*Primary Examiner* — Gregory J. Toatley, Jr.
*Assistant Examiner* — Amanda H Merlino
(74) *Attorney, Agent, or Firm* — Fredrikson & Byron, PA

(57) ABSTRACT

An optical detection sensor detects presence or absence of a product within a fluid delivery medium. An emitter directs radiation into the fluid delivery medium and detectors detect transmitted light at a plurality of wavelengths. The output of each detector and combinations of outputs of multiple detectors are associated with at least one out-of-product threshold. In addition, a color ratio is established. A controller compares the detector outputs and combination outputs with the associated out-of-product threshold(s). If any of the thresholds are satisfied, the controller compares the color ratio with an associated out-of-product threshold to verify an out-of-product event has occurred and reduce errors due to batch-to-batch variation of the product. The sensor is able to determine presence or absence of a variety of products having different color, transparency or turbidity.

25 Claims, 14 Drawing Sheets

U.S. PATENT DOCUMENTS

| | | |
|---|---|---|
| 5,141,871 A | 8/1992 | Kureshy et al. |
| 5,177,993 A | 1/1993 | Beckman et al. |
| 5,206,522 A | 4/1993 | Danby et al. |
| 5,455,423 A | 10/1995 | Mount et al. |
| 5,616,124 A | 4/1997 | Hague et al. |
| 5,672,887 A | 9/1997 | Shaw et al. |
| 5,680,111 A | 10/1997 | Danby et al. |
| 5,739,534 A | 4/1998 | Estenson |
| 5,754,767 A | 5/1998 | Ruiz |
| 6,101,452 A | 8/2000 | Krall et al. |
| 6,111,263 A | 8/2000 | Wahlberg |
| 6,489,896 B1 | 12/2002 | Platt et al. |
| 6,710,878 B1 | 3/2004 | Dean et al. |
| 6,851,453 B2 | 2/2005 | Lipscomb et al. |
| 6,896,159 B2 | 5/2005 | Crisp, III et al. |
| 6,969,865 B2 | 11/2005 | Duchon |
| 7,093,930 B2 | 8/2006 | Yildirim et al. |
| 7,141,037 B2 | 11/2006 | Butterfield et al. |
| 7,153,288 B2 | 12/2006 | Duchon et al. |
| 7,163,031 B2 | 1/2007 | Graves et al. |
| 2003/0025909 A1 | 2/2003 | Hallstadius |
| 2005/0195087 A1 | 9/2005 | Thompson et al. |
| 2005/0200848 A1 | 9/2005 | Levine |
| 2007/0114372 A1 | 5/2007 | Lievois |
| 2008/0134750 A1 | 6/2008 | Riley et al. |

FOREIGN PATENT DOCUMENTS

| | | |
|---|---|---|
| JP | 2-038842 | 2/1990 |

OTHER PUBLICATIONS

English-language abstract for JP2-038842 (Fujitsu Ltd).

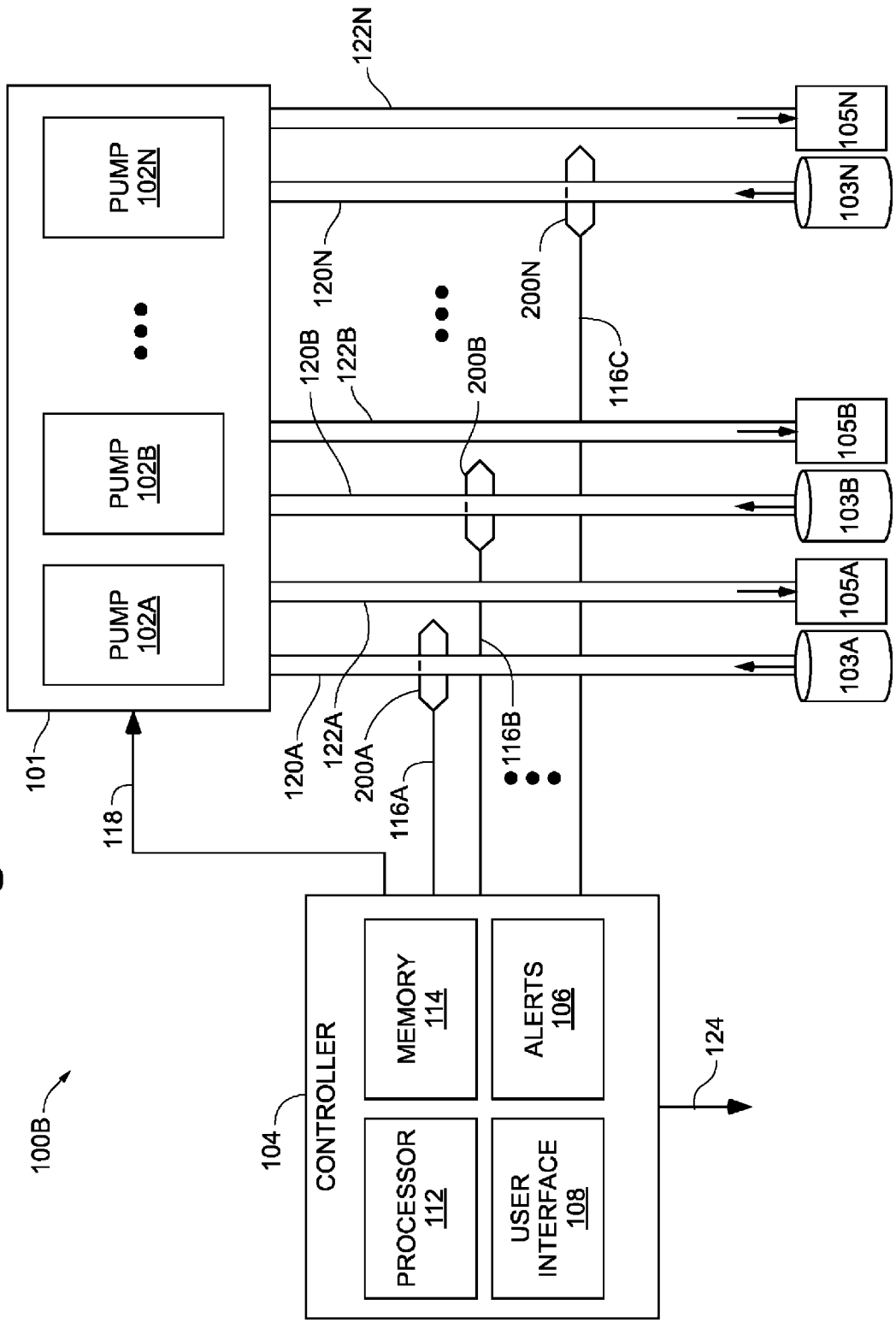

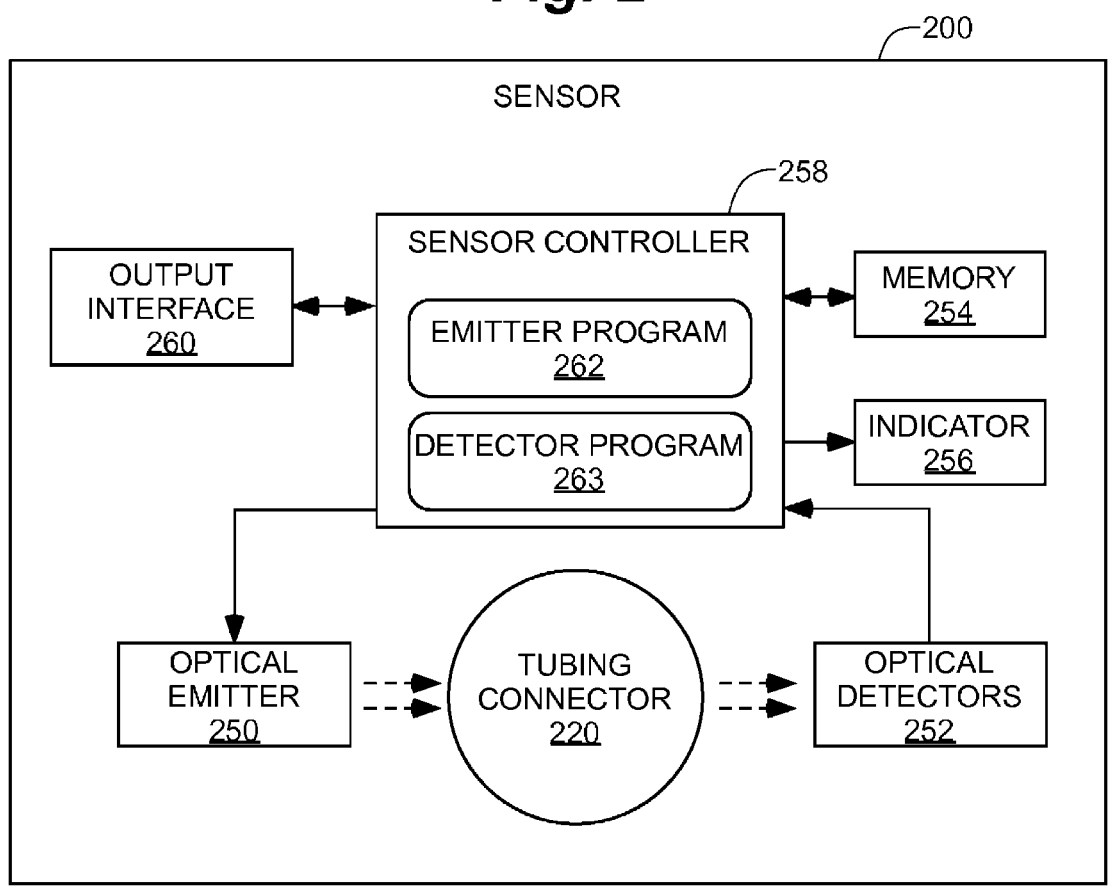

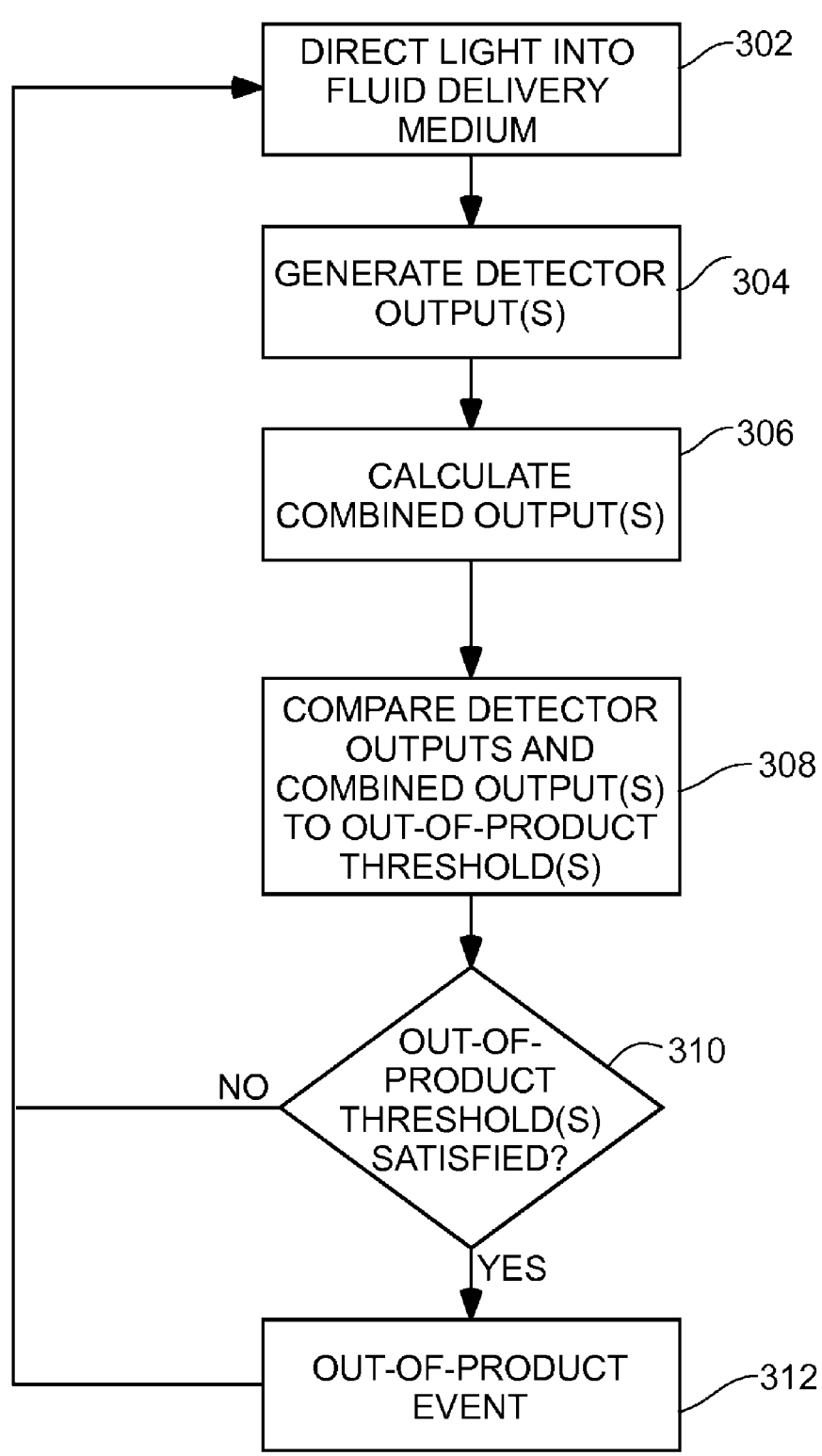

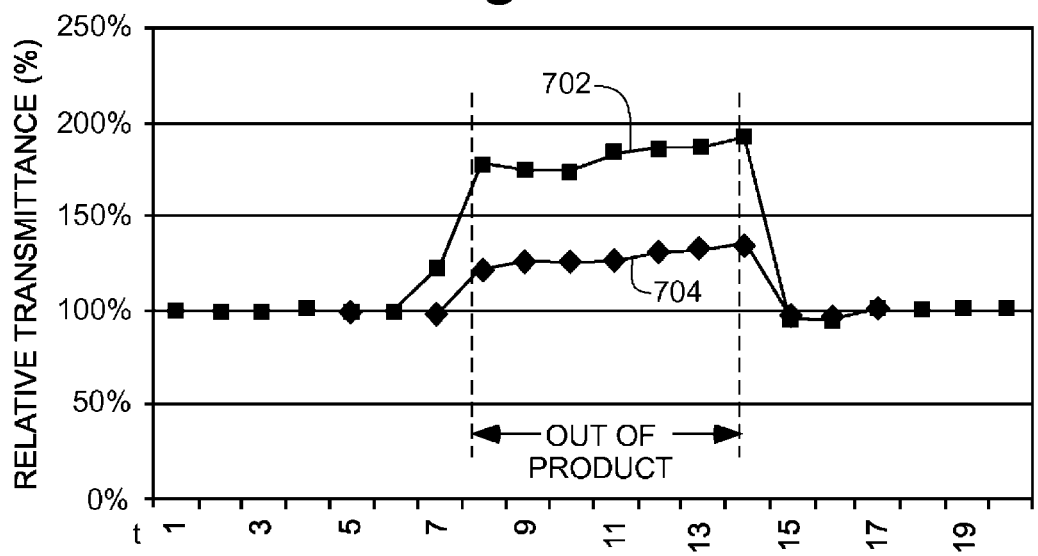
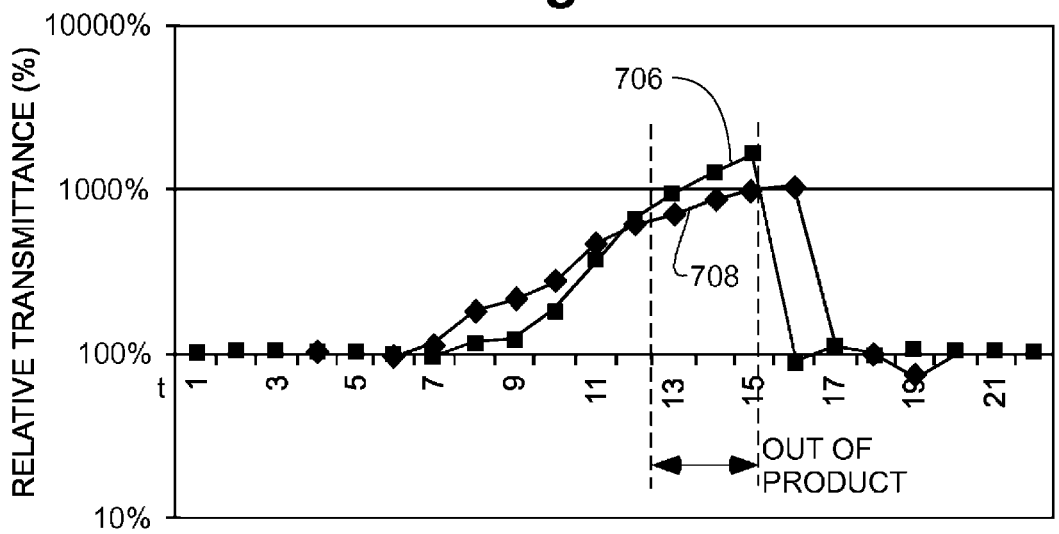

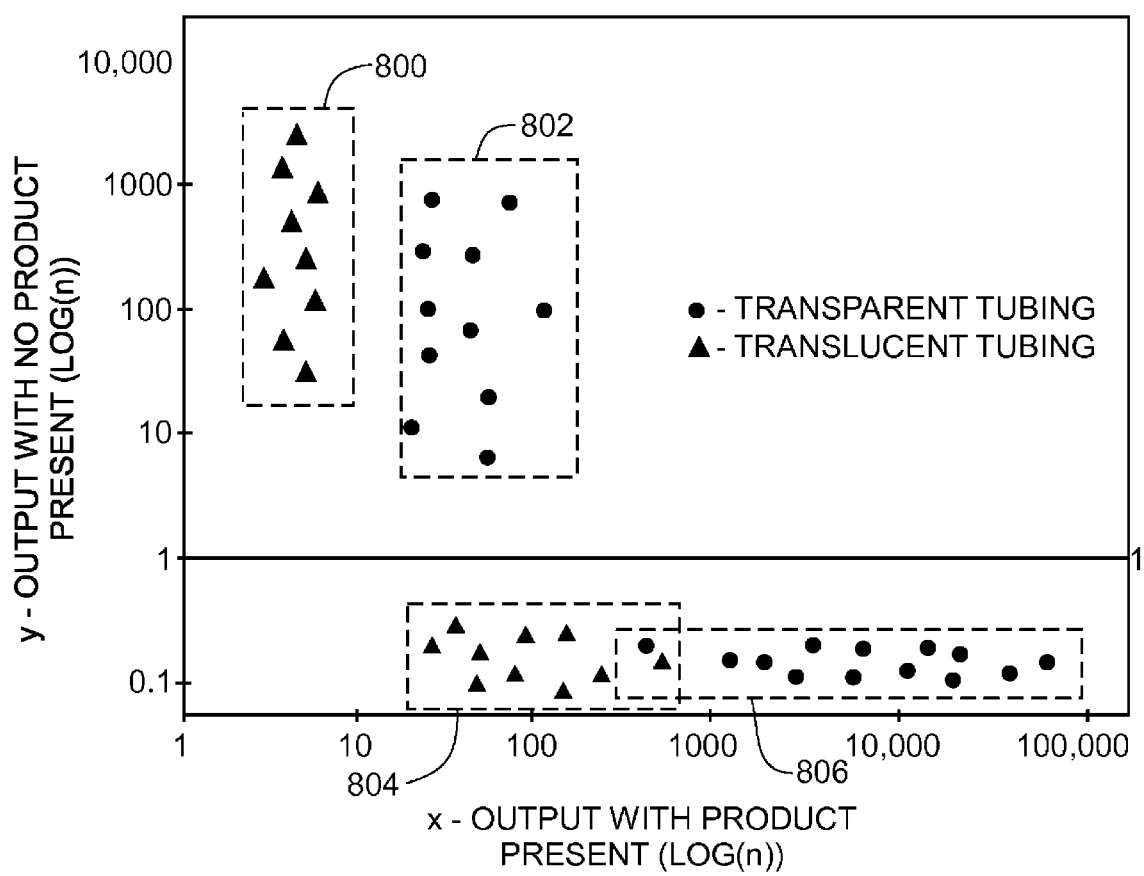

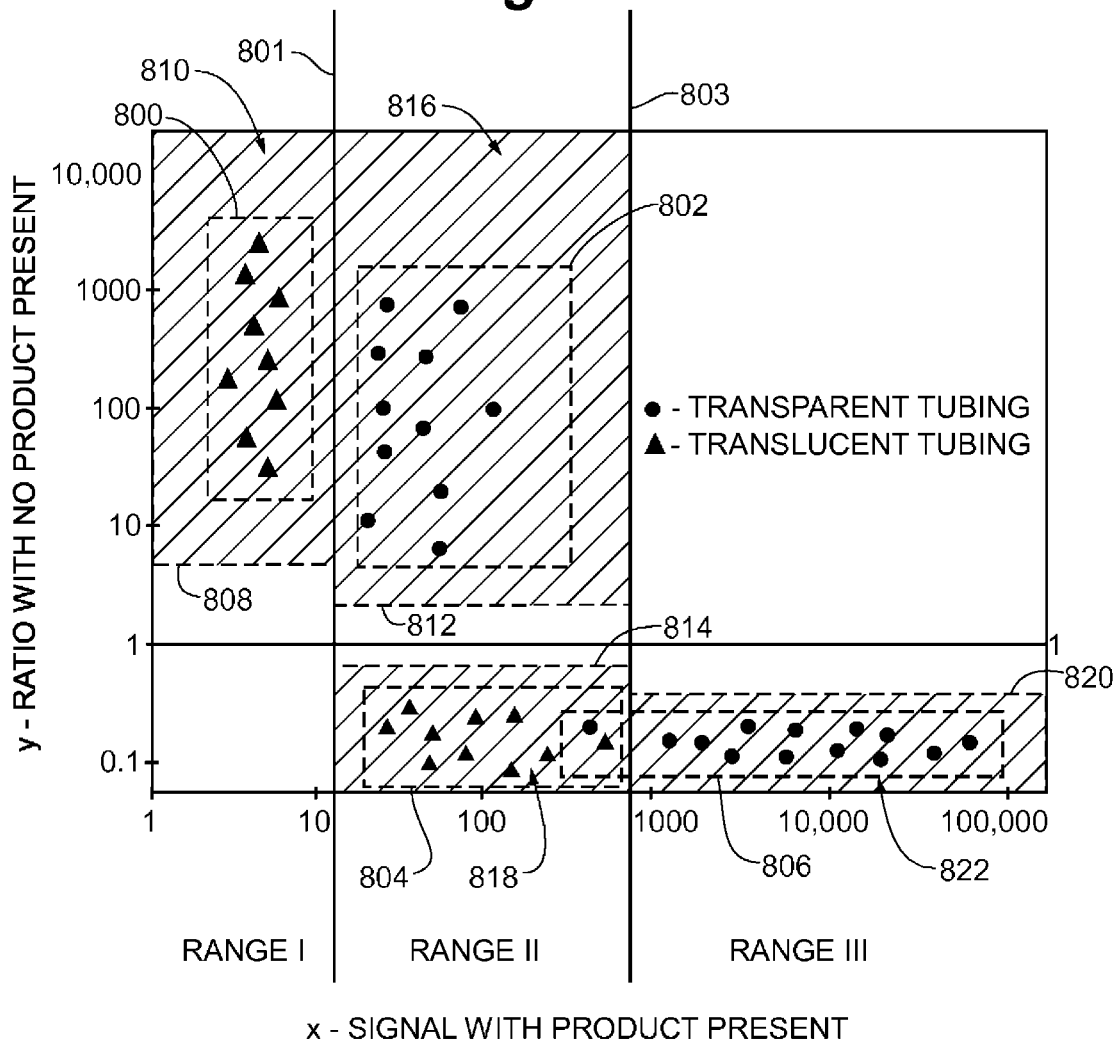

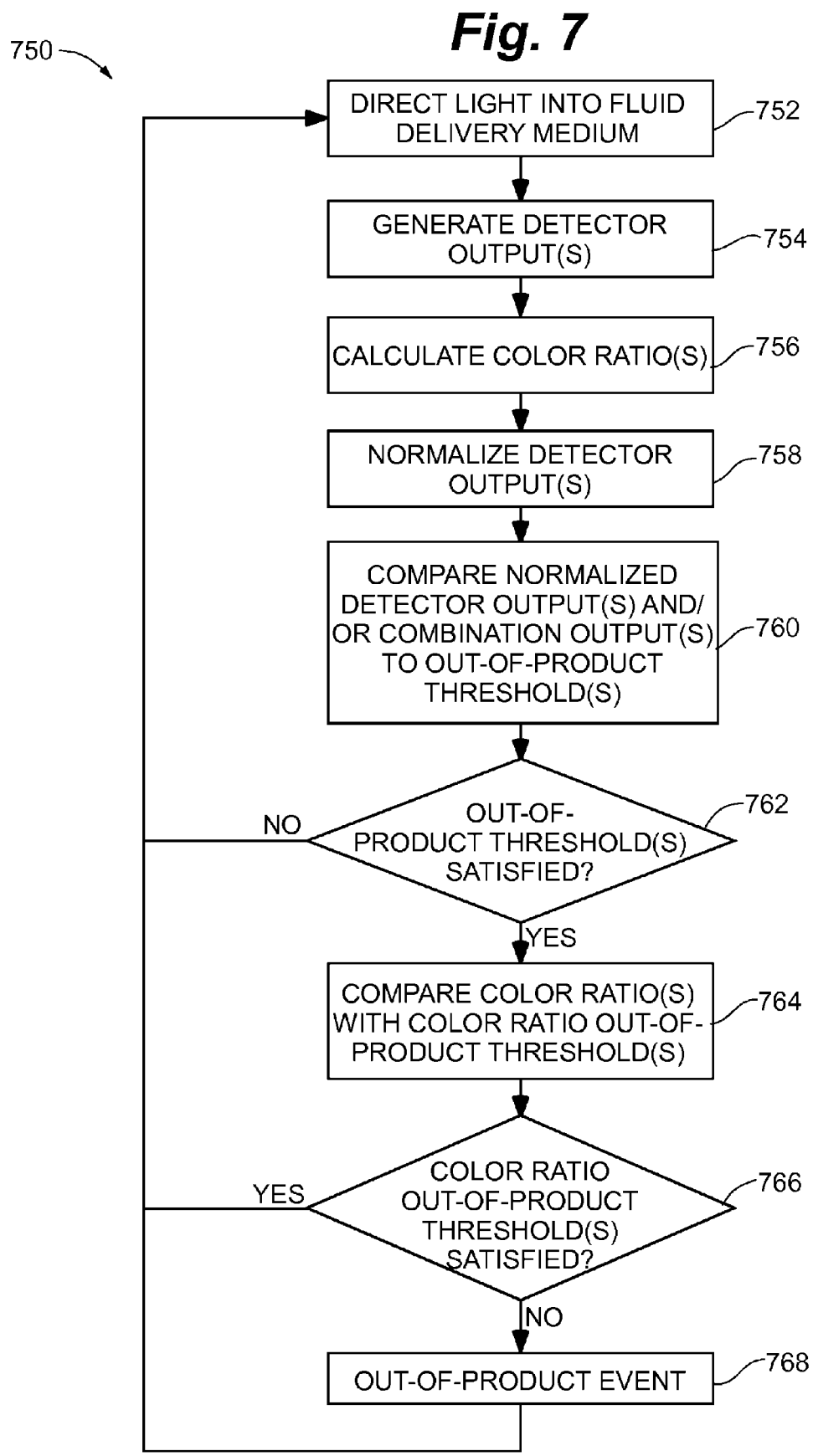

OPTICAL PRODUCT DETECTION SENSOR

CROSS-REFERENCE TO RELATED APPLICATION

This application is a continuation-in-part of U.S. patent application Ser. No. 12/247,743 filed Oct. 8, 2008, the entire content of which is incorporated herein by reference.

TECHNICAL FIELD

This application relates to the use of an optical detection sensor that detects presence or absence of a product in a fluid delivery medium.

BACKGROUND

Fluid dispensing systems typically deliver quantities of fluid to one or more components within the system. In certain fields, fluid dispensing systems may deliver small quantities of fluid. For example, in the medical field, a fluid dispensing system may be used to deliver small quantities of fluid into a patient's vascular system. However, in certain other fields, fluid dispensing systems may deliver larger quantities of fluid. For example, in a large-scale hotel or other laundry or restaurant facility, a fluid dispensing system may need to deliver large quantities of detergent, rinse agent, bleach or other cleaning agents on a continual basis.

A fluid dispensing system may include a pump and a product reservoir. The pump draws fluid from the product reservoir and delivers it to another component within the system. In certain cases, the pump may comprise a peristaltic-type pump, or another form of continuous pump. In other cases, the pump may comprise a form of positive-displacement pump. Many different forms of pumps may be used within a fluid dispensing system. In addition, the fluid dispensing system may include multiple different pumps within a pump assembly, or within multiple pump assemblies. Further, the fluid dispensing system may include a controller that controls operation of the one or more pumps within the system.

SUMMARY

In general, the invention relates to an optical detection sensor that detects the presence or absence of a product in a fluid delivery medium. For example, in a fluid dispensing system in which one or more products are delivered, one or more such sensors may be utilized to detect presence or absence of product within the fluid delivery medium. The sensor detects presence of absence of product in the fluid dispensing system and provides an out-of-product alert when absence of product is determined. The sensor may detect absence and/or presence of a variety of products having differing color, transparency or turbidity. Moreover, the sensor may detect absence and/or presence of products exhibiting variation in batch-to-batch color, transparency, or turbidity.

In one example, the invention is directed to a method comprising directing light into a fluid delivery medium in which presence or absence of a product is to be determined, detecting light in each of a plurality of wavelength ranges transmitted through the fluid delivery medium and producing therefrom a plurality of detector outputs, calculating at least one color ratio based on at least two of the detector outputs, normalizing each of the detector outputs, associating each of the normalized detector outputs with an out-of-product threshold, associating each of the color ratios with at least one color ratio out-of-product threshold, comparing, as an initial comparison, each of the normalized detector outputs with the associated out-of-product thresholds, and based on the initial comparison, either determining the presence of product within the fluid delivery medium or triggering a second comparison, wherein each of the color ratios are compared with the associated at color ratio out-of-product thresholds, the second comparison indicating whether product is present or absent within the fluid delivery medium.

In another example, the invention is directed to a sensor comprising an emitter that directs light into a fluid delivery medium in which presence or absence of a product is to be determined, a first detector that generates a first detector output based on detection of light within a first wavelength range transmitted through the fluid delivery medium, a second detector that generates a second detector output based on detection of light within a second wavelength range transmitted through the fluid delivery medium and a controller that calculates a combination output based on the first and second detector outputs, calculates a color ratio, compares the first detector output with at least one first out-of-product threshold, compares the second detector output with at least one second out-of-product threshold, compares the combination output with at least one combined out-of-product threshold, compares the color ratio with a color ratio out-of-product threshold, and determines presence or absence of the product within the fluid delivery medium based on the comparisons.

In another example, the invention is directed to a method comprising directing light into a fluid delivery medium in which presence or absence of a product is to be determined, generating a first detector output based on detected light within a first wavelength range transmitted through the fluid delivery medium, generating a second detector output based on to detected light within a second wavelength range transmitted through the fluid delivery medium, normalizing the detector outputs, calculating first and second combination outputs based on the first and second detector outputs, calculating a color ratio based on the first and second detector outputs, comparing the first normalized detector output with a first group of out-of-product thresholds, comparing the second normalized detector output with a second group of out-of-product thresholds, comparing the first combination output with a third group of out-of-product thresholds, comparing the second combination output with a fourth group of out-of-product thresholds, if any of the out-of-product thresholds of the first, second, third, or fourth groups of out-of-product thresholds are satisfied, comparing the color ratio with a fifth group of out-of-product thresholds, and determining presence or absence of product in the fluid delivery medium based on the comparisons.

The details of the invention are set forth in the accompanying drawings and the description below. Other features and advantages of the invention will be apparent from the description and drawings, and from the claims.

BRIEF DESCRIPTION OF DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

FIG. 1B is a diagram illustrating another example of a fluid dispensing system utilizing multiple optical sensors, each of which detects presence and/or absence of a different product to be dispensed.

FIG. 2 is a block diagram illustrating an example of an optical sensor that detects presence or absence of a product within a fluid delivery medium.

FIG. 3 is a flow diagram illustrating an example process by which an optical sensor detects presence or absence of a product within a fluid delivery medium.

FIGS. 5A-5D are graphs illustrating examples of detector outputs that may be generated by the detectors of an optical sensor.

FIGS. 6A-6C are graphs showing example experimental test data when product is absent from the fluid delivery tube for a variety of different products.

FIG. 7 is a flow diagram illustrating an example process by which an optical sensor can detect the presence or absence of a product within a fluid delivery medium incorporating a color ratio.

DETAILED DESCRIPTION

Figure 1A:
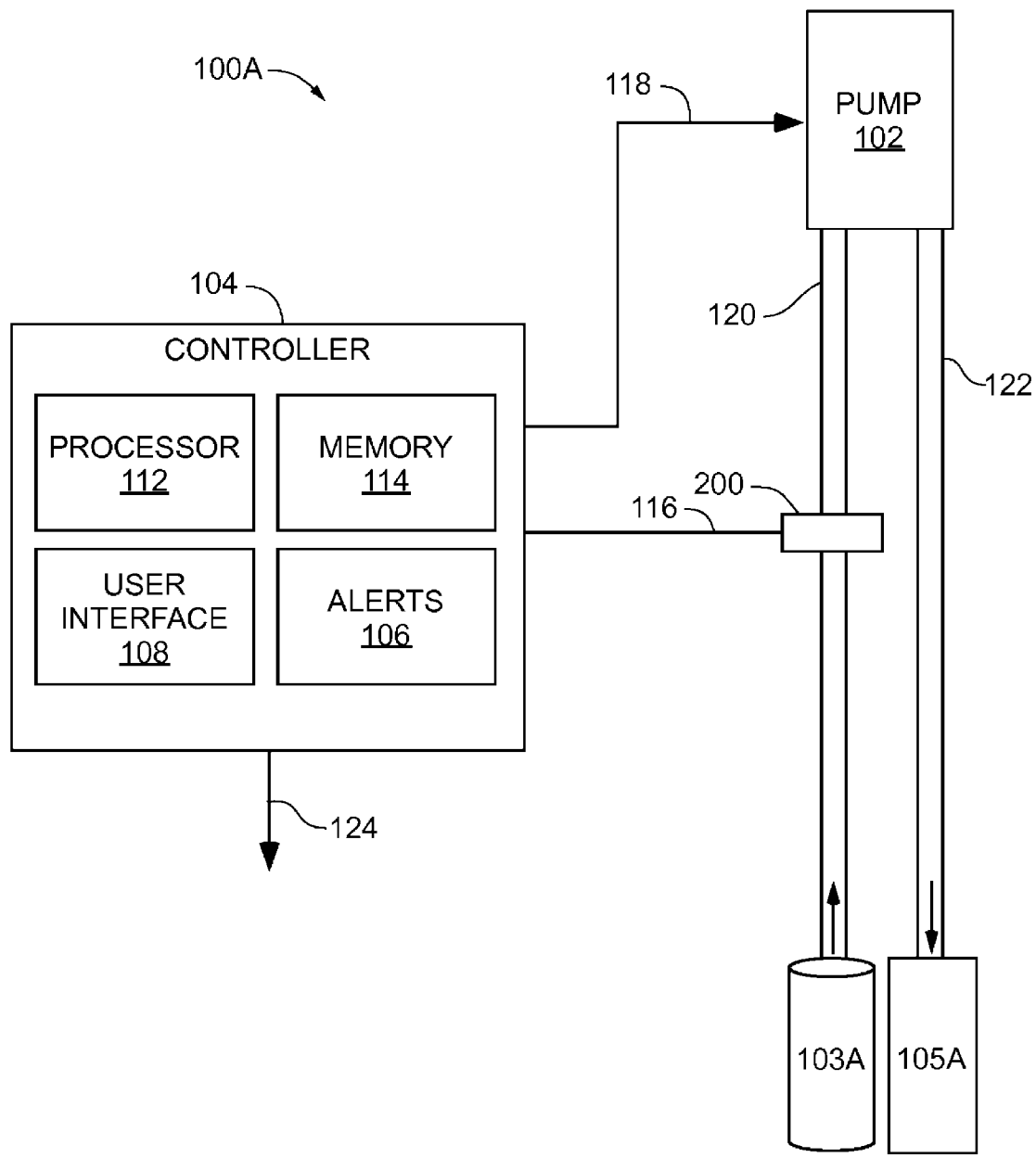
FIG. 1A is a diagram illustrating an example of a fluid dispensing system utilizing an optical sensor that detects presence and/or absence of a product to be dispensed.

FIG. 1A is a diagram illustrating an example fluid dispensing system 100A and an optical detection sensor 200 that detects presence and/or absence of a product to be dispensed. The sensor 200 may further generate an out-of-product alert and/or initiate a refill cycle when absence of the product is detected. Fluid dispensing system 100A includes a system controller 104, a pump 102 and a product reservoir 103. Pump 102 draws the product from reservoir 103 under control of system controller 104 and delivers the product to a dispensing site 105. Pump 102 draws product from product reservoir 103 through an input fluid delivery medium 120 and supplies fluid to dispensing site 105 via an output fluid delivery medium 122. Product reservoir 103 may contain any one of a multitude of different types of products having varying degrees of color, transparency and/or turbidity.

Controller 104 includes a processor 112, a user interface 108, a memory 114 and alerts 106. Controller 104 communicates with pump 102 via a connection 118. Depending upon the application, controller 104 may communicate with dispensing site 105 via another connection (not shown). Signals generated by sensor 200 are communicated to controller 104 via connection 116. Connection 116 may include, for example, a standard I2C connection. However, any appropriate connection/communication channel known in the art may be used. Controller 104 further includes at least one external connection 124 such as an internet, telephone, wireless or other connection for achieving external communication.

Memory 114 stores software for running system controller 104 and also stores data that is generated or used by processor 112. Processor 112 runs software stored in memory 114 to manage operation of system 104. User interface 108 may be as simple as a few user actuatable buttons or may include a display, a keyboard or keypad, mouse or other appropriate mechanisms for communicating with a user.

Dispensing site 105 may be an end use location of the product or may be some other intermediate location. For example, when fluid dispensing system 100A is used in a commercial laundry or kitchen application, dispensing site 105 may be a washing machine or dish machine, in which case the product(s) may be dispensed into an on-unit dispense mechanism or directly into the wash environment. In that example, the product(s) dispensed may include laundry or dish detergent, fabric softener, bleach, sanitizer, rinse agent, etc. As another example, when fluid dispensing system is used in a hotel, business, industrial or other application in which service employees perform cleaning duties, dispensing site 105 may be a bucket, pail or other vessel into which the product(s) are dispensed. Dispensing site 105 may also be a hose or other tubing from which the fluid(s) is directed to a desired location. It shall be understood that fluid dispensing system 100 may be used in many different applications in which fluid is dispensed and that the invention is not limited in this respect. Examples of applications in which fluid dispensing system 100 may be used include laundry applications, dishwashing applications, commercial cleaning operations, food preparation and packaging applications, industrial processes, healthcare applications, vehicle care applications, and others known in the art.

Input fluid delivery medium 120 and output fluid delivery medium 122 may be implemented using any type of flexible or inflexible tubing, depending upon the application. This tubing may be transparent, translucent, braided or other type of tubing. For simplicity and not by limitation, input fluid delivery medium 120 and output fluid delivery medium will be referred to herein as "input tubing 120" and "output tubing 122," respectively. Input tubing 120, output tubing 122 and pump 102 may be referred to herein as a "dispensing channel."

Pump 102 may be any form of pumping mechanism that supplies fluid from product reservoir 103 to dispensing site 105. For example, pump 102 may comprise a peristaltic pump or other form of continuous pump, a positive-displacement pump or other type of pump appropriate for the particular application.

In the example system shown in FIG. 1A, sensor 200 is positioned to detect presence and/or absence of product within input tubing 120. In operation, when fluid dispensing system attempts a dispensing cycle from a product reservoir 103 that has product remaining, input tubing 120 will likewise contain product. Sensor 200 obtains product presence information concerning presence of product within input tubing 120. Over time, as operation continues and more and more product is dispensed, product reservoir 103 becomes substantially empty. Because product is no longer available to dispense, input tubing 120 will likewise become substantially empty. When sensor 200 detects that the product presence information satisfies a set of predefined out-of-product thresholds, sensor 200 detects an absence of fluid within input tubing 200.

For purposes of the present description, an "out-of-product event" is defined as an event in which sensor 200 detects an absence of fluid within input tubing 200. In some embodiments, the "out-of-product event" is determined with respect to one or more predefined out-of-product thresholds. When sensor 200 detects an out-of-product event, sensor 200 may generate an out-of-product alert. The out-of-product alert may take the form of an out-of-product message to system controller 104. In response to the out-of-product message received from sensor 200, controller 104 may generate a visual and/or audible out-of-product alert (such as text or graphics with out accompanying sound, etc.) displayed on user interface 108. Alternatively or in addition, controller 104 may initiate and send an out-of-product message service call (such as via pager, e-mail, text message, etc.) to a technical service provider via external connection 124.

When an alert 106 is activated to indicate an out-of-product event, a user (such as an employee or service technician) may manually refill product reservoir 103. In this embodiment, the user may temporarily halt or shutdown operation of system 100A before refilling product reservoir 103. The user may manually do this by entering control commands via user interface 108 to stop operation of pump 102. After the user has refilled product reservoir 103, the user may manually re-start pump 102 and dispensing site 105, or may enter control commands via user interface 108 to cause controller 104 to send control signals via connection 118 to re-start pump 102. Controller 104 may further re-set, or clear, alerts 106 at the appropriate time (for example, after being manually cleared by a user, after product reservoir 103 has been refilled or system 100A is restarted).

In response to an out-of-product event, controller 104 may automatically stop pump 102 and/or dispensing site 105 when an out-of-product event is detected. In this embodiment, controller 104 may send control signals to pump 102 across connections 118 to temporarily stop operation of the corresponding components without user intervention. Controller 104 may then re-start pump 102 and/or dispensing site 105 after receiving input from the user that product reservoir 103 has been re-filled. Controller 104 may then send further control signals across connections 118 to restart pump 102. Alternatively, sensor 200 or controller 104 may initiate an automatic refill cycle after which the out-of-product alert would be cleared and the system started again.

Sensor 200 or system controller 104 may also generate a visual indicator that indicates presence of fluid within input tubing 120. For example, a light of one color, such as green, may be used to indicate that product reservoir 103 has product remaining, while a light of another color, such as red or blinking, may be used to indicate that product reservoir 103 is empty and needs to be refilled.

FIG. 1B is a diagram illustrating another example fluid dispensing system 100B. Fluid dispensing system 100B dispenses multiple products. To that end, fluid dispensing system 100B includes multiple product channels (A-N), each having associated product reservoirs 103A-103N, pumps 102A-102N, system controller 104 and dispensing sites 105A-105N. Pumps 102A-102N are included in pump assembly 101. Pumps 102A-102N draw in fluid from a respective product reservoir 103A-103N through an input tubing 120A-120N, and supply fluid to one of dispensing sites 105A-105N through output tubing 122A-122N. Each product reservoir 103A-103N may contain any of a multitude of different types of products having varying color, transparency and/or turbidity. Optical detection sensors 200A-200N detect presence and/or absence of the product dispensed in the respective each dispensing channel.

Although the example fluid dispensing system 100B shown in FIG. 1B shows each dispensing channel as having its own dedicated product reservoir 103, input tubing 120, output tubing 122, pump 102, destination site 105 and sensor 200, it shall be understood that there need not be a one to one correspondence for each dispensing channel. For example, sensors 200A-200N may be implemented in a single unit through which the input tubing for each dispensing channel is routed. Alternatively, various combinations of one channel per sensor or two or more channels per sensors may also be used and the invention is not limited in this respect.

Likewise, the example pump assembly 101 of FIG. 1B includes multiple pumps 102A-102N, one for each dispensed product. It shall be understood, however, that there need not be a one to one correspondence between pumps 102A-102N and the dispensing channels. For example, some dispensed products may share one or more pumps, which are switched from one dispensed product to another under control of system controller 104. The pump or pumps 102A-102N provide fluid to the appropriate dispensing site 105 from one of product reservoirs 103A-103B.

It shall also be understood that any of sensors 200A-200N may also be positioned to detect presence and/or absence of product within output tubing 122A-122N rather than input tubing 120A-120N as shown in FIG. 1B, and that the location of sensors 200A-200N may be more a matter of convenience than of system performance.

Controller 104 is coupled to pump assembly 101 via connection 121. Through connection 121, controller 104 is able to communicate with pump assembly 101 and effectively communicate and/or control operation of each individual pump 102 (e.g., to temporarily stop or start operation, as described previously in reference to FIG. 1A). Depending upon the application, controller 104 may also communicate with one or more dispensing sites 105A-105N.

Each sensor 200A-200N detects presence and/or absence of fluid within the corresponding input tubing 120A-120N. Controller 104 is coupled to each sensor 200A-200N via a corresponding connection 116A-116N. Controller 104 monitors the signals received from each sensor 200A-200N, and may respond as described above to any detected out-of-product events. For example, controller 104 may generate a visual or audible alert 106 or display a message on user interface 108 if one or more of the sensors 200A-200N has detected an out-of-product event. The visual or audible alert 106 and/or message displayed on user interface 108 and/or message sent via pager, e-mail or text message, etc. would indicate which of product reservoirs 103A-103N is empty, thus informing a user which product reservoir needs to be filled. Controller 104 may also automatically temporarily stop and then re-start the pump 102A-102N corresponding to the empty product reservoir 103A-103N and/or may initiate an automatic refill cycle of the empty product reservoir as described above.

Although in FIG. 1B each sensor is shown with a dedicated connection to controller 104, it shall be understood that sensors 200A-200N may be connected to communicate with controller 104 in any of several different ways. For example, sensors 200A-200N may be connected to controller 104 in a daisy-chain fashion. In this example, controller 104 is coupled directly to a first sensor 200A via connection 116 and each subsequent sensor 200B-200N is coupled the next sensor, etc. A communication protocol to identify and communicate separately with each sensor 200A-200N may also be used. It shall be understood, however, that the invention is not limited with respect to the particular architecture by which sensors 200A-200N are connected with and communicate with controller 104, and that the system may be set up in many different ways known to those of skill in the art.

FIG. 2 is a block diagram illustrating an example embodiment of a sensor 200 that detects presence and/or absence of a product to be dispensed. Sensor 200 includes a controller 258, a memory 254, an optical emitter 250 and one or more optical detectors 252. Sensor 200 also includes at least one external connector 260 and a tubing connector 220. Sensor 200 may also include an optional indicator 256. The components of sensor 200 may be implemented on a single printed circuit board (PCB) or may be implemented using two or more PCB boards. Sensor 200 communicates with external devices, such as controller 104 or other sensors via connector 250.

Memory 254 stores software and data used or generated by controller 258. As will be discussed in more detail below, memory may store baseline detection values produced by detectors 252 and processed by controller 258. During operation of sensor 200, controller 258 may control indicator 256 based upon information received from optical detectors 252. For example, upon detection of an out-of-product event controller 258 may cause indicator 256 to generate a visual or audible alert. Controller 258 may additionally send an out-of-product message to an external device, such as controller 104, via connector 260.

Optical emitter 250 includes at least one optical emitter that emits radiation having a specified wavelength range. Emitter 250 may emit light within a narrow-band of wavelengths or a relatively broader range of wavelengths. Emitter 250 may also emit light having varying wavelength over time.

In one example, emitter 250 emits light within the visible spectrum. Light within the visible spectrum includes wavelengths in the range from 380 nm to 720 nm. One example of such an emitter is a white LED (light-emitting diode) model NFSL036LT available from Nichia Corporation. It shall be understood however, that emitter 250 may also be implemented using other light sources, such as a surface mount full color LED NSCM315CT available from Nichia Corporation. Several individual LEDs placed in close proximity could also be used. Light emitted by emitter 250 propagates through tubing that runs through tubing connector 220 of sensor 200 and may be detected by one or more optical detectors 252. The amount of radiation detected by detectors 252 depends on the contents of the tubing running through tubing connector 220 and also on the type of tubing. If the tubing contains liquid product, detectors 252 will detect a certain level of radiation emitted from emitter 250. However, if the tubing is substantially empty, detectors 252 may detect a different amount of radiation emitted from emitter 250.

Optical detectors 252 include at least one optical detector that detects radiation within associated wavelength ranges within the visible light spectrum. Detectors 252 may be implemented using multiple detectors, one for each wavelength range or may be implemented using a detector or detectors that are programmable to detect multiple wavelength ranges. The terms "detector" and "detectors" will therefore be used interchangeably herein.

Detector(s) 252 detect radiation that is emitted by emitter 250 and that has propagated through tubing running through sensor 200 (via tubing connector 220). For example, detector (s) 252 may include a blue photodetector that detects visible light within all of part of the blue wavelength range, and a red photodetector that detects visible light within all or part of the red wavelength range. Blue light within the visible spectrum includes wavelengths of approximately 420 nm-480 nm, whereas red light includes longer wavelengths of approximately 620 nm-680 nm. When emitter 250 is a full color LED or RGB LED (for example NSCM315CT) which emits red (630 nm), green (520 nm) and blue (470 nm) peaks, detectors 252 may include a non-selective silicon photodiode that detects light within all visible range. It shall be understood, however, that detectors 252 may include detectors in other wavelength ranges, and that the wavelength ranges chosen for both the emitter 250 and the detectors 252 may depend upon the color, transparency and/or turbidity of the products to be detected by sensor 200.

Controller 258 controls operation of emitter 250 and receives signals concerning the amount of light detected from detectors 252. Controller 258 executes an emitter program 262 to control emitter 250, and executes detection program 263 to process signals received from detectors 252. If detection program 263 detects an out-of-product event, it may activate indicator 256 and/or send a corresponding out-of-product message to an external device via connector 260.

In one embodiment, detection program 263 may also initiate indicator 256 and/or send a corresponding output message if it confirms presence of fluid within the tubing.

In one example, controller 258 initiates emitter program 262 and detection program 263 to create baseline detection data when product is present. When an external controller, such as controller 104, is informed that product is present within tubing, controller 104 may send a baseline command to the sensor 200 (via connector 260) to cause generation of such baseline data. Controller 104 may be so informed, for example, via manual input from a user. When controller 258 of sensor 200 processes the baseline command, it will execute emitter program 262 to emit light and also execute detection program 263 to obtain baseline data from detectors 252. Upon receipt of the baseline detection data from detectors 252, controller 258 may store the baseline data within memory 254. If multiple detectors are used within detectors 252, signals for each detector may be stored in memory 254. Such baseline data may later be used for normalization purposes when attempting to determine absence and/or presence of fluid within the tubing.

Optical detectors 252 detect the amount of emission radiated by emitter 250 propagated through tubing and the contents of the tubing. Controller 258 compares the amount of light received by detectors 252 to the baseline data. Changes from the baseline data that satisfy a threshold may be caused by air present in the tubing, such as when product reservoir 103 is substantially empty and no product is available. Accordingly, some changes that satisfy a threshold may be indicative of an out-of-product event. However, not all changes from the baseline are due to an out-of-product event. For example, ambient lighting conditions, product and tubing variation, and batch-to-batch variation of a single product can all contribute to or create significant variation from the baseline which can trigger false positive out-of-product events. Some embodiments include additional features to avoid such instances.

Controller 258 may include an ambient filter function. Different levels of ambient light may affect the amount of light detected by sensor 200. To address this issue, controller 258 may execute emitter program 262 to turn on emitter 250 for a determined period of time (e.g., 1 second) in a first phase, and turn off emitter 250 for a determined period of time (e.g., 1 second) in a second phase. Emitter program 262 may execute these first and second phases over one or more cycles. A detection signal generated when emitter 250 is turned off may be attributed to ambient light. This signal may be subtracted from a detection signal generated when emitter 250 is turned on to account for ambient light. By obtaining detection information from detectors 252 during one or more cycles, detection program 263 and controller 258 may account for ambient light.

In addition, in some embodiments, the sensor 200 or controller 258 may scale the detection signal so that sensor-to-sensor variation can be eliminated. Often, the absolute output generated by one sensor unit may vary when compared to the absolute output generated by a second sensor unit even when testing an identical substance under identical conditions.

Accordingly, some sensors or controllers incorporate a predetermined scaling coefficient that translates the raw, absolute detection signals, into scaled detector output. For example, raw sensor data can be scaled according to a multiplicative scaling coefficient as follows, $$U_x\text{Color} = (\text{Color Detector Absolute Output}) * (\text{Color Scale Coefficient}), \text{ where}$$

UxColor is the scaled detector output for a given color (Color);

Color Detector Absolute Output is the raw, absolute detection signal produced by the sensor in response to the detected light of a given color (Color); and Color Scale Coefficient is the scale coefficient associated with a particular detector for a given color (Color).

Each sensor 200 thus can be associated with a scale coefficient (Color Scale Coefficient) that linearly scales the raw detection data supplied by that sensor to a uniform scale. The scale coefficient can be factory calibrated, for example, by taking controlled detector readings of a standardized test solution, e.g. water in a standardized tube, e.g. EVA tubing, and under uniform testing conditions (i.e. lighting, temperature, etc.). The scale coefficient can then be determined by setting the scaled detector output equal to a prescribed value, e.g. 8000, and solving the above equation for Color Scale Coefficient. Thus, as used in this application, the term "detector output" should be interpreted to include both raw detection signals, and scaled detector output.

Controller 258 processes the detector outputs received from detectors 252 to determine whether an out-of-product event has occurred. For example, detection program 263 may calculate two normalized detector outputs, RatioRed (corresponding to the normalized detector output of a red detector), RatioBlue (corresponding to the normalized output of a blue detector), and at least one so-called combination output, Xs, as follows:

$$RatioRed=(UcRed-UdRed)/(UnRed-UndRed);$$

$$RatioBlue=(UcBlue-UdBlue)/(UnBlue-UndBlue);$$
and $$Xs=RatioRed \times RatioBlue, \text{ where}$$

Uc is the current detector output (emitter on);
Ud is the current detector output (emitter off);
Un is the baseline detector output when fluid is present (emitter on);
Und is the baseline detector output when fluid is present (emitter off);
RatioRed is the normalized ratio of the current output of the red detector to the baseline output of the red detector when fluid is present, corrected for ambient light;
RatioBlue is the normalized ratio of the current output of the blue detector to the baseline output of the blue detector when fluid is present, corrected for ambient light; and
Xs is a combination output, in this case the product of the normalized current output of the red and blue detectors, RatioBlue and RatioRed.

As shown from these calculations, detection program 263 may account for ambient light by subtracting detector outputs obtained when the emitter is off. Detection program also normalizes the detector outputs using baseline data previously obtained with product present within the tubing.

In this example, the combination output Xs is the product of normalized detector outputs RatioRed and RatioBlue. However, other or additional combination outputs may be calculated using other mathematical operations that generate useful measures of product presence or absence. For example, other combination outputs may be obtained using summation, subtraction, derivation, integration and other mathematical operations. It shall therefore be understood that the present invention is not limited to use of the particular combination output Xs, but that additional or other combination outputs are also within the scope of the present invention.

Detection program 263 compares one or more of the normalized detector outputs and/or the combination outputs with at least one out-of-product threshold to determine presence and/or absence of product within the tubing. For example, if any of these values (RatioRed, RatioBlue, or Xs) satisfies one or more out-of-product thresholds, as described in further detail below, detection program 263 may determine that there is no product present in the tubing, and detect an out-of-product event.

Each detector and combination output is associated with at least one out-of-product threshold. Associating each detector and combination output with multiple out-of-product thresholds helps to ensure that out-of-product events are detected for a variety of products having differing color, transparency and/or turbidity, as well as for different types of tubing (e.g., transparent, translucent, braided, etc.). This enables a single sensor 200 to be used for a variety of products. For example, detector program 263 may include at least one red detector out-of-product threshold, at least one blue detector out-of-product threshold and at least one combined (e.g., Xs or other combination) out-of-product threshold. When sensor 200 includes detectors operating in other wavelength ranges, detector program 253 may include an out-of-product threshold or thresholds corresponding to those detected ranges as well.

In one example, if the detector output RatioRed satisfies the at least one red out-of-product threshold, detection program 263 generates an out-of-product event. Likewise, if the detector output RatioBlue satisfies the at least one blue out-of-product threshold or the combination output Xs satisfies the at least one combined out-of-product threshold, detection program 263 generates an out-of-product event. The out-of-product thresholds are predetermined and stored in memory 254. As described in more detail below, the out-of-product thresholds may be determined empirically based upon experimental test data or upon expert knowledge that has been stored within memory 254.

FIG. 3 is a flow diagram illustrating an example process (300) by which sensor 200 determines presence and/or absence of a product. Emitter 250 directs light into a fluid delivery medium in which presence or absence of product is to be determined (302). Emitter 250 may include, for example, a white LED that emits white light in the visible wavelength range.

Detectors 252 generate detector outputs based upon detection of light in their associated wavelength range transmitted through the fluid delivery medium (304). For example, detectors 252 may include a first detector that generates a first detector output corresponding to emitted light within a first wavelength range transmitted through the fluid delivery medium. Detectors 252 may further include a second detector that generates a second detector output corresponding to emitted light within a second wavelength range transmitted through the fluid delivery medium.

Detectors 252 may also include additional detectors that generate detector outputs based on an amount of light received in additional wavelength ranges. Sensor 200 may utilize these additional (i.e., third, fourth, etc.) detector outputs depending upon the color, transparency and/or turbidity of the products to be analyzed. Alternatively, a single detector may generate all or a subcombination of the detector outputs.

Controller 258 executes detection program 263 to calculate any combination outputs that may be indicative of an out-of-product event (306). For example, detection program may calculate the combination output Xs described above, which is a combination of the normalized red detector output RatioRed and the normalized blue detector output RatioBlue.

Detector outputs may be combined in other ways to produce other combination outputs to ensure accuracy of out-of-product detection for a variety of different products and/or different tubing.

Controller 258 executes detection program 263 to compare the detector output(s) and the combination output(s) with at least one corresponding out-of-product threshold(s) to determine presence or absence of product within the fluid delivery medium (308). For example, as described above, detection program 263 may calculate values RatioRed, RatioBlue, and Xs. If any of these detector outputs satisfies its corresponding out-of-product threshold(s) (310), detection program 263 detects an out-of-product event (312).

For example, detection program 263 may compare a first detector output (e.g., RatioRed) to one or more first out-of-product thresholds (308). Detection program 263 may also compare a second detector output (e.g., RatioBlue) to one or more second out-of-product thresholds, which may or may not be different from the first out-of-product thresholds (308). Detection program 263 may also compare at least one combination output (e.g., Xs or other combination outputs) to one or more combined out-of-product thresholds, which may or may not be different from the first or second out-of-product thresholds (308). Additional detector outputs or combination outputs may also be used. If at least one of these comparisons indicates that a detector output satisfies a corresponding out-of-product threshold (310), detection program 263 detects an out-of-product event (312).

In another example, one or more color ratios may be incorporated into the detection program 263. A "color ratio" is an example of another calculation that can be performed by the controller 258. However, the term "color ratio" as used herein should not be confused with a "combination output," e.g. Xs above or Ys below. Where "combination outputs" are based on some combination of normalized detector outputs, e.g. RatioRed and RatioBlue, "color ratios" are based upon current (non-normalized) detector outputs. For example, a red-blue color ratio may be calculated as follows:

$$\text{ColorRatio} = (U_c\text{Red} - U_d\text{Red})/(U_c\text{Blue} - U_d\text{Blue}),$$
where Uc is the current detector output (emitter on);
Ud is the current detector output (emitter off).

As with detector and combination outputs, each color ratio is associated with at least one out-of-product threshold. These color ratio out-of-product thresholds can be empirically predetermined and stored in memory 254. However, the comparison of a color ratio and its associated out-of-product threshold can, in some embodiments, occur at a separate step from other comparisons in the detection program 263 as described below.

FIG. 7 is a flow diagram illustrating an example process (750) including the use of one or more color ratios by which sensor 200 determines presence and/or absence of a product. As above, emitter 250 directs light into a fluid delivery medium in which presence or absence of product is to be determined (752). Emitter 250 may include, for example, a white LED that emits white light in the visible wavelength range.

Detectors 252 generate detector outputs based upon detection of light in their associated wavelength range transmitted through the fluid delivery medium (754). For example, detectors 252 may include a first detector that generates a first detector output corresponding to emitted light within a first wavelength range transmitted through the fluid delivery medium. Detectors 252 may further include a second detector that generates a second detector output corresponding to emitted light within a second wavelength range transmitted through the fluid delivery medium.

Detectors 252 may also include additional detectors that generate detector outputs based on an amount of light received in additional wavelength ranges. Sensor 200 may utilize these additional (i.e., third, fourth, etc.) detector outputs depending upon the color, transparency and/or turbidity of the products to be analyzed. Alternatively, a single detector may generate all or a subcombination of the detector outputs.

Controller 258 executes detection program 263 to calculate color ratios indicative of the ratio of current detector outputs (756). For example, detection program may calculate the red-blue color ratio ColorRatio described above, which is a ratio of the current red detector output UcRed and the current blue detector output UcBlue accounting for ambient effects UdRed and UdBlue.

Additionally, controller 258 normalizes detector outputs based upon the baseline detector readings (758). For example, detection program 263 may calculate RatioRed and RatioBlue, as described above.

In some embodiments, controller 258 may additionally calculate combination outputs (step not shown). Such combination output calculation step is analogous to the combined output calculation step (306) described above with reference to the process (300) illustrated in FIG. 3. As above, any combination of outputs that may be indicative of an out-of-product event may be calculated. For example, in some embodiments, a product combination Xs is calculated as above. In addition, in some embodiments a ratio combination Ys is calculated according to the following:

$$Ys = \text{RatioRed}/\text{RatioBlue}, \text{ where}$$

Ys is a combination output, in this case the normalized current output of the red detector RatioRed divided by the normalized current output of the blue detector RatioBlue.

Controller 258 executes an initial comparison step (760) to compare the detector output(s) and, optionally, the combination output(s), with at least one corresponding out-of-product threshold(s). For example, as described above, detection program 263 may calculate values RatioRed, RatioBlue, Xs, and Ys. If, during the initial comparison (760) any of these outputs satisfies its corresponding out-of-product threshold(s) (762), the detection program 263 proceeds to a second comparison (764). If none of the outputs satisfy the associated out-of-product threshold(s) (762), the presence of product within the fluid delivery medium is confirmed, and the process (750) restarts.

For example, detection program 263 may compare a first detector output (e.g., RatioRed) to one or more first out-of-product thresholds (760). Detection program 263 may also compare a second detector output (e.g., RatioBlue) to one or more second out-of-product thresholds, which may or may not be different from the first out-of-product thresholds (760). Detection program 263 may also compare at least one combination output (e.g., Xs, Ys, or other combination outputs) to one or more combined out-of-product thresholds, which may or may not be different from the first or second out-of-product thresholds (760). Additional detector outputs or combination outputs may also be used. If at least one of these comparisons indicates that a detector output satisfies a corresponding out-of-product threshold (310), detection program 263 proceeds to the second comparison (764).

At the second comparison, the detector program 263 compares one or more of the color ratios with the associated out-of-product threshold (764). For example, a process 750 which calculated red-blue color ratio ColorRatio (756) could compare the red-blue color ratio with the associated out-of-product threshold from memory 254. At this comparison stage, however, if the color ratio satisfies the associated out-of-product threshold, the detector program 263 determines that there is product present within the fluid delivery medium, and the process (750) restarts. If the color ratio does not satisfy the associated out-of-product threshold, the detector program 263 determines the absence of product from the fluid delivery medium, and an out-of-product event is triggered (768).

Figure 4A:
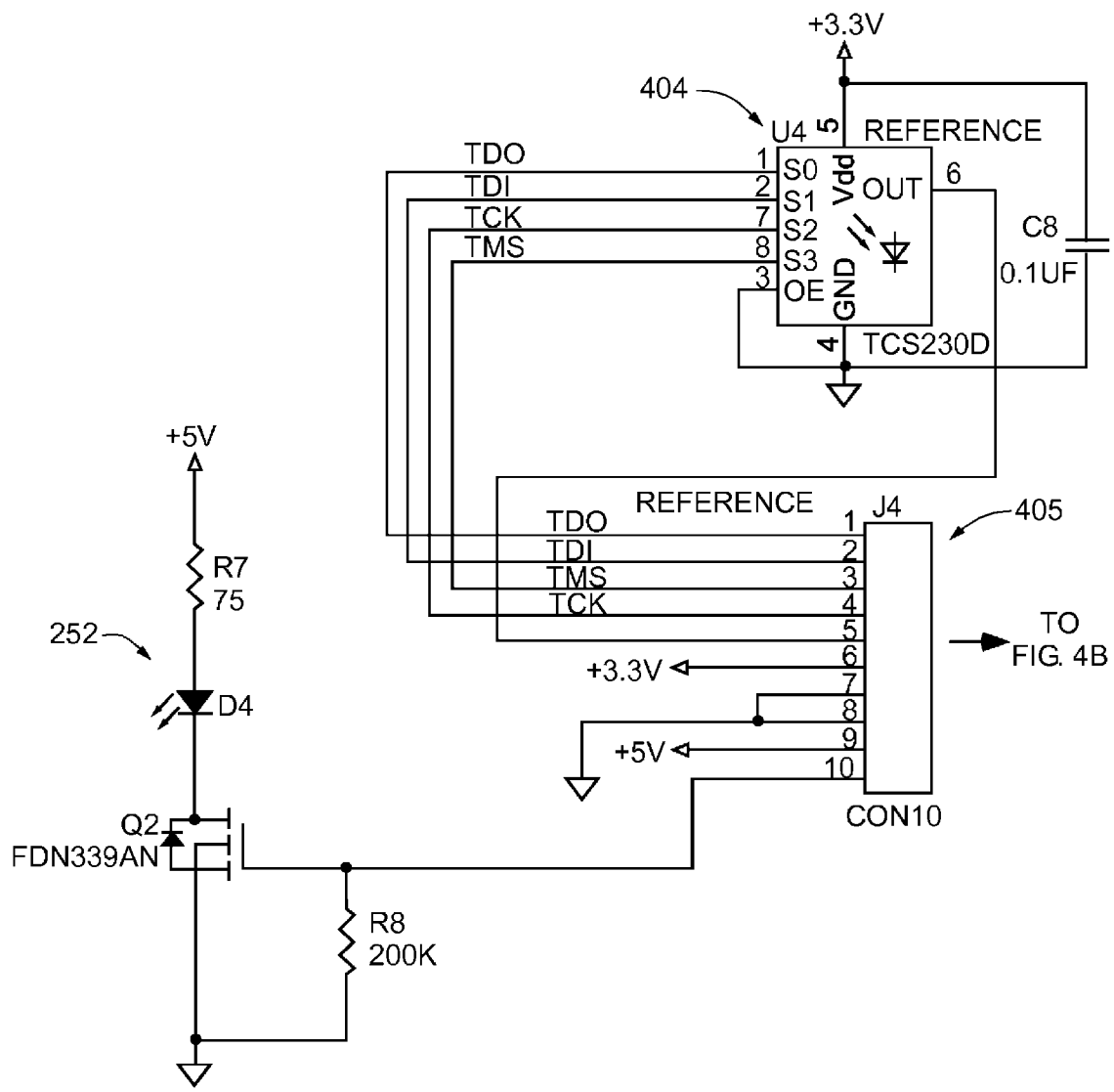
FIG. 4A-4B are schematic diagrams illustrating an example optical sensor.
Figure 4B:
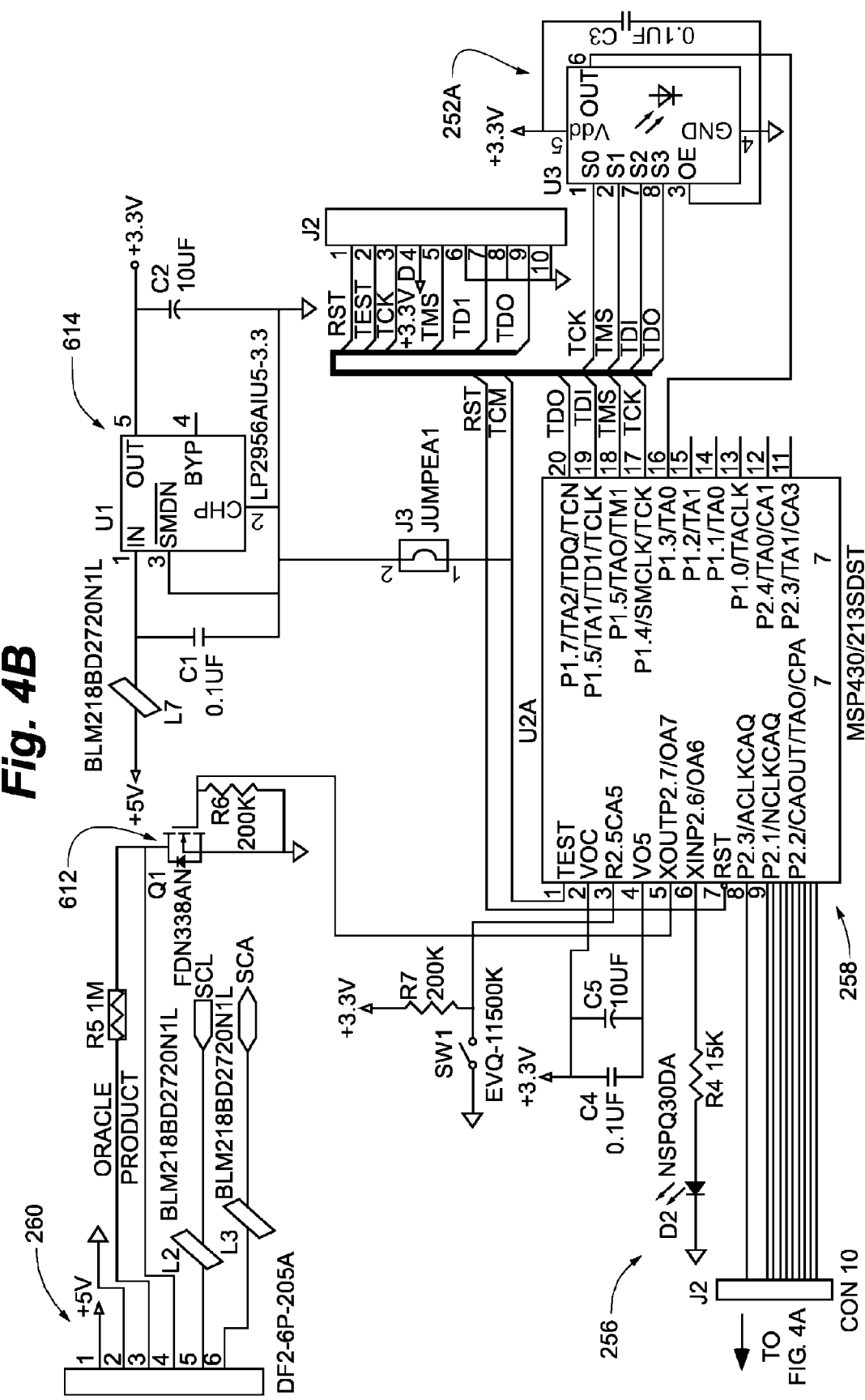

FIGS. 4A-4B are a schematic diagram illustrating an example sensor 200 that detects presence and/or absence of a product. Although particular component values are shown in FIGS. 4A-4B, it shall be understood that all values displayed in FIG. 4, including resistance, capacitance, and/or power supply values, are exemplary only, and that the invention is not limited in this respect. Other component values may be used in other embodiments without departing from the spirit or scope of the present invention.

FIG. 4A illustrates an example optical emitter 250 and associated circuit components of an example sensor 200. In this example, emitter 250 is a white LED, such as white LED model NFSL036LT available from Nichia Corporation. A reference detector 404 and a controller interface 405 are also shown in FIG. 4A. Emitter 250 is powered with a +5V power supply, which may be provided by a power supply of sensor 200, or may be provided by an external component, such as controller 104 or other external device. Operation of emitter 250 is controlled by emitter program 262 of sensor controller 258. For example, sensor controller 258 may alternately cycle emitter 250 on and off by controlling a switch labeled Q2 in FIG. 4 to account for ambient light as described above.

An optional reference detector 404 monitors the amount of light emitted by emitter 250 and generates a corresponding reference signal. Reference detector 404 includes chip "U4" that includes a reference photodetector. Over time, the output of emitter 250 may vary due to factors such as use and wear of emitter 250. Reference detector 404 provides feedback to controller 258 regarding the level of radiation emitted by emitter 250. Controller 258 may then use this reference information to monitor the status of emitter 250, during execution of detection program 263, and may also provide this reference information to detectors 252.

For example controller 258 may receive reference signal from reference detector 404 when a new LED is installed as emitter 250. Controller 258 may store this baseline detection information, in one embodiment, within memory 254. Controller 258 may also provide this baseline information to optical detectors 252. Over time, the radiation from emitter 252 may decrease. Reference detector 404 detects this change and provides reference information to controller 258, and may also provide it to detectors 252. Controller 258 may compare the most recent reference information provided by reference detector 404 with the previously stored (baseline) information to provide normalization for detection program 263. In this fashion, detection program 263 can adjust for varying output from emitter 252 over time while consistently and reliably determining presence or absence of product within fluid tubing.

Controller interface 405 is the interface from emitter 250 to controller 258. Controller interface 405 includes a connector labeled J4 in FIG. 4A. Connector J4 may be part of the same PCB as emitter 250 or may be located on a separate PCB. Connector J4 connects to the rest of the sensor 200 circuit components via connector J2 as shown in FIG. 4B.

FIG. 4B shows an example embodiment of sensor controller 258, optical detector 252, indicator 256 and output interface 260. FIG. 4B also shows a switch 612 and a power supply 614. In this example, optical detectors 252 produce outputs (on pin 6 labeled "OUT" in this example) having a frequency that is directly proportional to the detected light intensity in the selectable wavelength ranges. In one example, detector 252 is programmed to detect alternatively visible light in the red wavelength range of 600-750 nm or in the blue wavelength range of 400-500 nm. In this example, detector 252 is a programmable color light to frequency converter TCS230 available from Texas Advanced Optical Solutions Corporation of Plano, Tex. However, it shall be understood that other wavelength ranges and detectors could also be used, and that the invention is not limited in this respect.

As is shown in FIG. 4B, detector 252 is connected to sensor controller 258. Detector 252 may or may not be located on the same PCB as sensor controller 258, and the invention is not limited in this respect. Sensor controller 258 determines the wavelength range (e.g., color) of detector 252 via inputs S0-S3 (pins 1, 2, 7 and 8, respectively in this example). Detector 252 generate a detector output (OUT) that is provided to sensor controller 258 for processing.

In the embodiment of FIG. 4B, sensor 200 includes an indicator 256, in this case an LED. When, for example, sensor controller 258 detects an out-of-product event based upon detection signals received from detector 252, sensor controller 258 may actuate indicator 256. The actuation of indicator 256 provides visual notice to a user that an out-of-product event has occurred.

Sensor controller 258 may generate and send one or more signals to an external device when it has detected an out-of-product event. To that end, sensor controller 258 may provide output signals via switch 612 to output interface 610. Output interface 610 may be coupled a matching connector (such as connector 260 of FIG. 2) which allows sensor 200 to communicate with an external device, such as external controller 104 (FIGS. 1A-1B) or other external device.

Through output interface 610, sensor controller 258 may provide both a logical and a digital output signal to indicate an out-of-product event. For example, the logical output signal may comprise a drain output signal in the range of 3.3V-10V As another example, the digital output signal may comprise an I2C digital signal. It shall be understood, however, that the output signal may be implemented in other ways, and that the invention is not limited in this respect.

FIGS. 5A-5D are graphical diagrams illustrating example detector outputs that may be generated by optical detector 252. FIGS. 5A-5D show a percent (relative) of the strength of the detection signals from each of a red and a blue detector normalized to the baseline values (e.g., RatioRed and RatioBlue) on the y-axis versus time on the x-axis. In these examples, blue and red detectors are chosen due to the difference in transmission of blue and red light for many colored products. Blue light includes wavelengths in the range of approximately 420 nm-480 mm, whereas red light includes longer wavelengths in the range of approximately 620 nm-680 nm Use of multiple detectors allows sensor 200 to detect presence and/or absence of many different liquid products having varying color, transparency or turbidity. To generate the data shown in FIGS. 5A-5B substantially transparent tubing was used as the fluid delivery medium. However, the fluid delivery medium need not be entirely transparent. For example, translucent, braided or other tubing may also be used.

FIG. 5A shows a graph of example detector outputs signals generated by a blue detector (702) and a red detector (704) for a first colored product. During the time interval between t=0 and t=6 (on the x-axis), blue detector output 702 and red detector output 704 are substantially equal. During this time interval, both detectors detect presence of fluid within the fluid delivery medium. However, starting at approximately t=6, both blue detector output 702 and red detector output 704 begin to increase. This is indicative of the fluid delivery medium becoming empty. Detector outputs 702 and 704 continue to increase until approximately time t=8 and then remain at a relatively higher level (with blue detector output 702 remaining relatively higher than red detector output 704) until approximately time t=14. Between t=14 and t=15, detector outputs 702 and 704 both decrease until they reach substantially the same levels as prior to t=6. This decrease indicates that the fluid delivery medium is no longer empty (in other words, the product reservoir has been refilled or product has been otherwise introduced into the fluid delivery medium). Thus, between time t=7 and t=13 (approximately), both detection signals show a marked increase in signal strength. Depending on the out-of-product threshold(s) used and the detection program 263 executed by controller 258, sensor 200 may detect an out-of-product event during the time frame from approximately t=7 to t=15, for example. Controller 258 may use detector outputs from detectors 252 to make a number of calculations to detect an out-of-product event (e.g., RatioRed, RatioBlue and/or other detector outputs, Xs, Ys and/or other combination outputs, ColorRatio and/or other color ratios) as described above with respect to FIGS. 3 and 7.

FIG. 5A shows that, for the first colored fluid, the detector outputs from both the blue detector and the red detector increase when the fluid delivery medium becomes empty. FIG. 5A also shows that the blue detector begins to detect an absence of fluid in the fluid delivery medium slightly earlier than does the red detector. In addition, when the fluid delivery medium becomes empty, the blue detector output increases more than the red detector output. In the example shown in FIG. 5A, depending upon the out-of-product thresholds set and the detection program 263 executed by controller 258, either both the red and blue detector outputs might indicate an out-of-product event, or only the blue detector output might indicate an out-of-product event.

FIG. 5B shows a graph illustrating example detector outputs generated from both a blue detector and a red detector for a turbid product. Signal 706 represents the output of the blue detector and signal 708 represents the output of the red detector. At approximately time t=6, both the blue detector output 706 and the red detector output 708 begin to increase, as the fluid delivery medium starts to become empty. Both signals 706 and 708 appear to hit their respective peaks between t=14 and t=15 (approximately), after which point in time both graphs decrease sharply. Depending on the out-of-product thresholds used and the detection program 263 executed by controller 258, sensor 200 may generate one or more detector outputs to controller 104 (FIGS. 1A-1B) indicating an out-of-product event during the time frame t=12 to t=15, for example.

FIG. 5B shows that, for the example turbid product, detection signals from both the blue detector and the red detector increase, but more gradually than occurred with the first colored product of FIG. 5A, when the fluid delivery medium has less product, or is empty. FIG. 5B also shows that, when the fluid delivery medium has less product, or is empty, the blue detection signal and the red detection signal increase in similar fashions for this example turbid product.

Figure 5C:
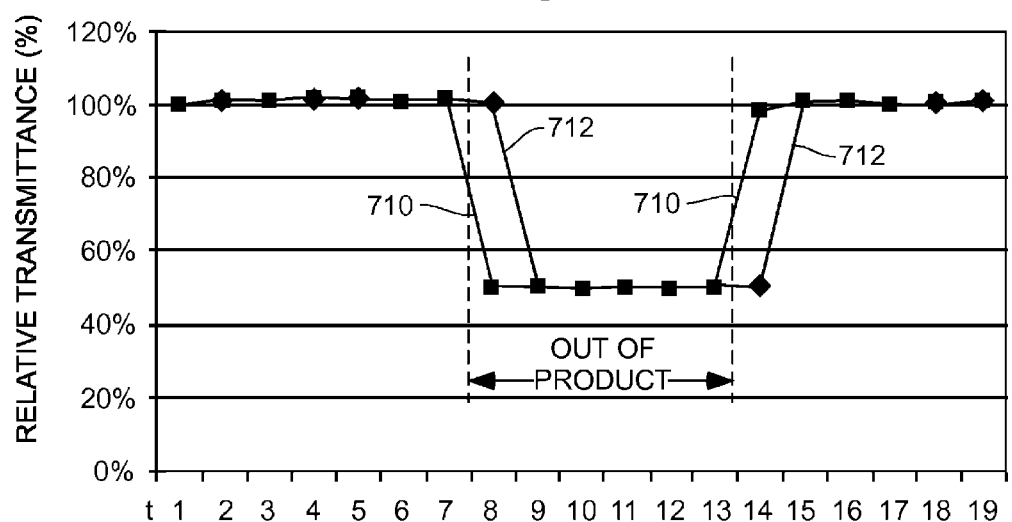

FIG. 5C shows a graph illustrating example detector outputs generated from a blue detector and a red detector for a transparent product. Signal 710 represents the output of the blue detector and signal 712 represents the output of the red detector. At about t=6, when the fluid delivery medium starts to become empty, blue detector output 710 begins to quickly decrease.

Slightly later, after about t=7, red detector output 712 begins to decrease. At about t=13, signal 710 begins to rise while, slightly later, signal 712 begins to rise, when the product is again present within the fluid delivery medium. Depending on the out-of-product thresholds used and the detection program 263 executed by controller 258, sensor 200 may generate one or more out-of-product messages to controller 104 (FIGS. 1A-1B) indicating an out-of-product event during the time frame t=7 to t=13, for example.

FIG. 5C shows that, for this example transparent fluid, detection signals from both the blue detector and the red detector decrease when the fluid delivery medium has less product, or is empty. FIG. 5C also shows that the blue detector begins to detect an absence of fluid in the fluid delivery medium slightly earlier than does the red detector for this example transparent product.

Figure 5D:
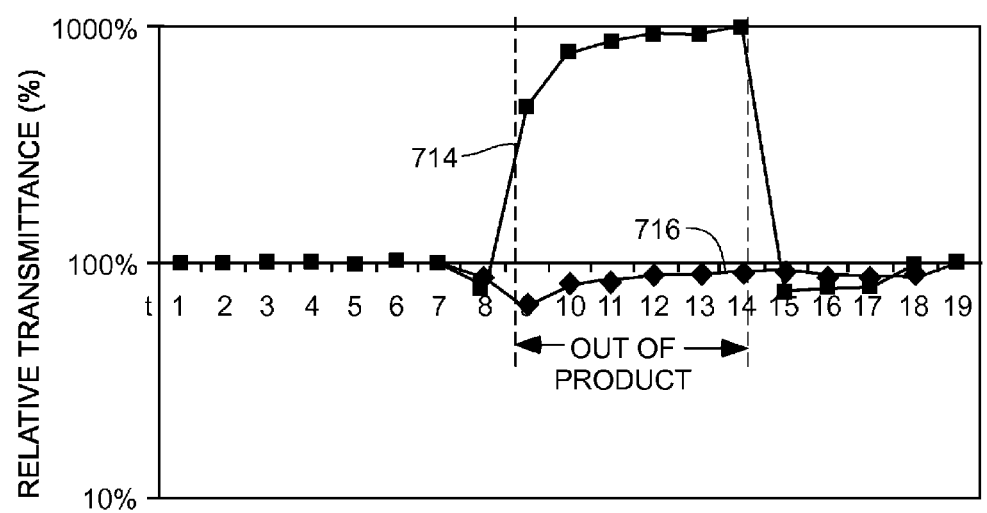

FIG. 5D shows a graph illustrating example detector outputs generated from both a blue detector and a red detector for a second colored product. Signal 714 represents the output of the blue detector and signal 716 represents the output of the red detector. In this example, only the blue detection signal increases when the fluid delivery medium has less product or is empty.

This provides an example of when one type of detector may detect an out-of-product event while the other may not. As shown in FIG. 5D, blue detector output 714 markedly increases starting at about t=8 and controller 258 may use this detected increase in signal strength from the blue detector to identify an out-of-product event.

It should be noted that the graphical diagrams are shown in FIGS. 5A-5D for exemplary purposes only. Various other forms of detector outputs (having different graphical profiles) may be generated when detecting different fluids, and the detector outputs will depend upon the color of the fluid, the turbidity of the fluid and/or the transparency of the fluid.

To detect out-of-product events for a variety of products, the processing carried out by sensor controller 258 must account for the multiple different detector outputs which can occur with different products, some examples of which were explained above with respect to FIGS. 5A-5D. To that end, sensor 200 may include more than one detector to detect light of different wavelengths transmitted through the product. For example, as described above, sensor 200 may include a red detector and a blue detector. Sensor 200 may also calculate combination outputs.

For example Xs, the product of RatioRed and RatioBlue in the example given above, because it is a product of two detector outputs, may exceed an out-of-product threshold for Xs at times when either one or both of RatioRed or RatioBlue do not exceed their own out-of-product thresholds. By combining more than one detector and by calculating several detector outputs and combining them in different ways, accuracy of detection of out-of-product events for a variety of different products having differing color, transparency and turbidity is increased.

Additionally, system accuracy and robustness can be improved by the introduction of a color ratio comparison as a second point of comparison. As described above, with reference to FIG. 7, a color ratio comparison (764) can be performed following the identification of a detector or combination output which satisfies the associated out-of-product threshold (762). It has been found that the inclusion of this color ratio comparison can improve sensor performance leading to the occurrence of fewer false positives and false negatives. In particular, batch-to-batch variation within a product can lead to large variations in detector and combination outputs. For example, in some products, normalized detector and combination outputs can vary by a factor of 5 or more between batches of the same product. However, batch-to-batch color ratios remain significantly more stable from batch-to-batch. Accordingly, including the color ratio comparison can reduce the occurrence of false positives in some embodiments.

Figure 6C:
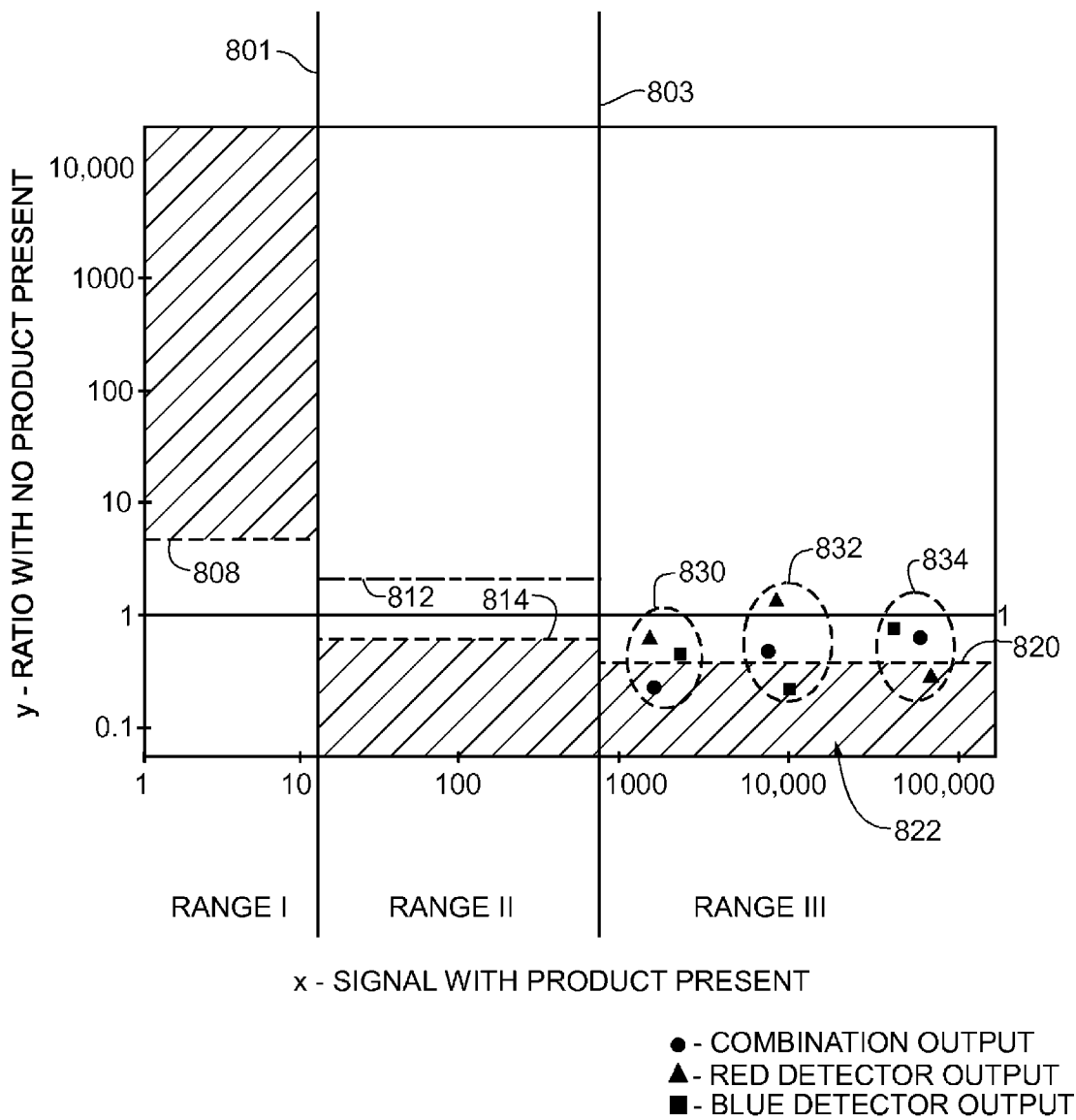

FIGS. 6A-6C are graphs showing example experimental test data when product is absent from the fluid delivery tube for a variety of different products. FIG. 6A is a graph showing example test data that may be used to empirically determine the out-of-product thresholds or ranges to be used by controller 258 during out-of-product detection calculations. The graph of FIG. 6A plots the signal output of one of the color ranges (or channels) of detector 252 (e.g., a red detector or a blue detector, for example) when product is present (the baseline) on the x-axis and the ratio of output for the same detector when product is absent (e.g., Ratio output=[signal from detector when no product present]/[signal from detector when product is present]) on the y-axis. Both the x- and y-axis are shown using a logarithmic scale. The line labeled "1" on the y-axis represents a 1:1 ratio of the measured detector output to the baseline; in other words, the output that would be detected when product is present.

As indicated in FIG. 6A, the each circular data point corresponds to an output of the detector for a different one of a variety products using transparent tubing, and each triangular data point corresponds to an output of the detector for a different one of the same variety of products using translucent tubing. It should be noted that while each product is represented by a single circular or triangular data point, batch-to-batch variation of each of the products may ultimately result in each product occupying a range covering a plurality of data points rather than the single data point as indicated.

In FIG. 6A, the majority of test points fall into four distinct areas: areas 800, 802, 804 and 806. The variance of the test data may be due to the type of fluid being detected (e.g., variations in color, transparency, turbidity) and the type of tubing (e.g., transparent or translucent). From FIG. 6A, it may be concluded that if a data point falls within one of areas 800, 802, 804 or 806, or falls outside of a limit defined by either area 800, 802, 804 or 806, an out-of-product condition will be detected.

FIG. 6A illustrates that the areas of data shift to the left depending upon whether transparent tubing or translucent tubing is used. For example, the data falling in area 806 for transparent tubing shifts to the left and falls in area 804 for translucent tubing. Similarly, the data falling in area 802 for transparent tubing shifts to the left and falls in area 800 for translucent tubing. From this test data, out-of-product thresholds for the relevant detector may be empirically determined so that out-of-product events are detected for a variety of different products and for both transparent and translucent tubing.

Similar graphs may be generated for each color range of detectors 252 and the associated out-of-product thresholds for color range of detector 252. Similar graphs may also be calculated for the combination outputs, such as Xs, which is calculated by multiplication of normalized outputs for different colors, and Ys which is calculated as the ratio of normalized outputs for different colors, or other mathematical combinations, and the associated out-of-product thresholds for those combined responses empirically determined as well. Likewise, similar graphs may also be calculated for the color ratios, such as the red-blue color ratio ColorRatio discussed above. It shall be understood, therefore, that FIG. 6A is one example of such a graph, and that other graphs may be generated for each color range of detector 252 in the system and for each combination output calculated and used during processing for the out-of-product determination.

FIG. 6B shows the same graph as FIG. 6A and also illustrates an example division of the x-axis into three ranges, Range I, Range II and Range III. Boundaries 801, 803 of these ranges may be determined empirically using the data points to correspond to the majority of out-of-product events detected for a variety of products having different color, transparency or turbidity, as well as for different types of tubing, such as transparent or translucent.

Each range in FIG. 6B is associated with at least one out-of-product threshold. For example Range I is associated with an out-of-product threshold 808. In this example, when the detector output is greater than out-of-product threshold 808, the out-of-product threshold is deemed to be "satisfied" and an the out-of-product event may be detected based upon the particular detection program 263 being implemented. Shaded region 810 indicates the area of Range I in which an out-of-product event may be detected.

Range II is associated with two out-of-product thresholds 812 and 814. In this example, when the detector output is greater than out-of-product threshold 812, or less than out-of-product threshold 814, the out-of-product threshold is deemed to be "satisfied" and an the out-of-product event may be detected based upon the particular detection program 263 being implemented.

Shaded regions 816 and 818 indicate the areas of Range II in which an out-of-product event may be detected.

Range III is associated with an out-of-product threshold 820. In this example, when the detector output is less than out-of-product threshold 820, the out-of-product threshold is deemed to be "satisfied" and an the out-of-product event may be detected based upon the particular detection program 263 being implemented. Shaded region 822 indicates the area of Range III in which an out-of-product event may be detected.

In this way, each color range (or channel) for detector 252 is associated with at least one out-product-threshold, and the out-of-product thresholds associated with each detector may be experimentally determined to correspond to the majority of out-of-product events for a variety of products having different color, transparency or turbidity, and to minimize the potential for false positives and/or false negatives. Those skilled in the art will readily recognize that the example threshold values given herein and the relative magnitude of the out-of-product thresholds shown in FIG. 6B are given only for purposes of example, and that the invention is not limited in this respect. The thresholds for each color range for detector 252 and in each range may vary from sensor to sensor, and may also vary depending upon the specific product or group of products to be detected. The thresholds should be chosen such that detection of false positives by sensor 200 is minimized, and such that failure to detect out-of-product events when they do occur (i.e., false negatives) is also minimized.

Figure 8A:
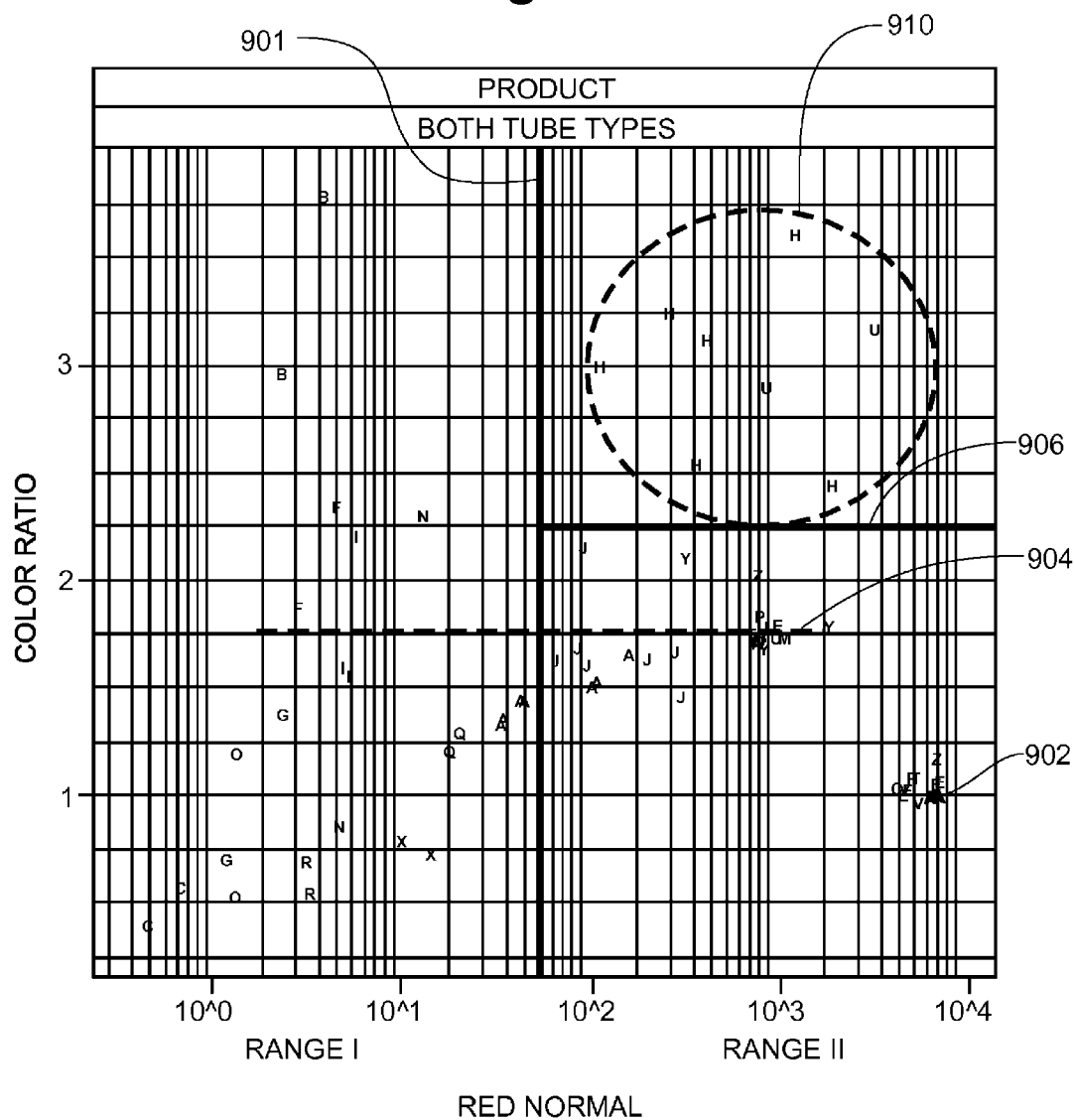
FIGS. 8A and 8B are graphs illustrating example experimental color ratio test data when product is present (FIG. 8A) and absent (FIG. 8B) from the fluid delivery medium for a variety of different products.
Figure 8B:
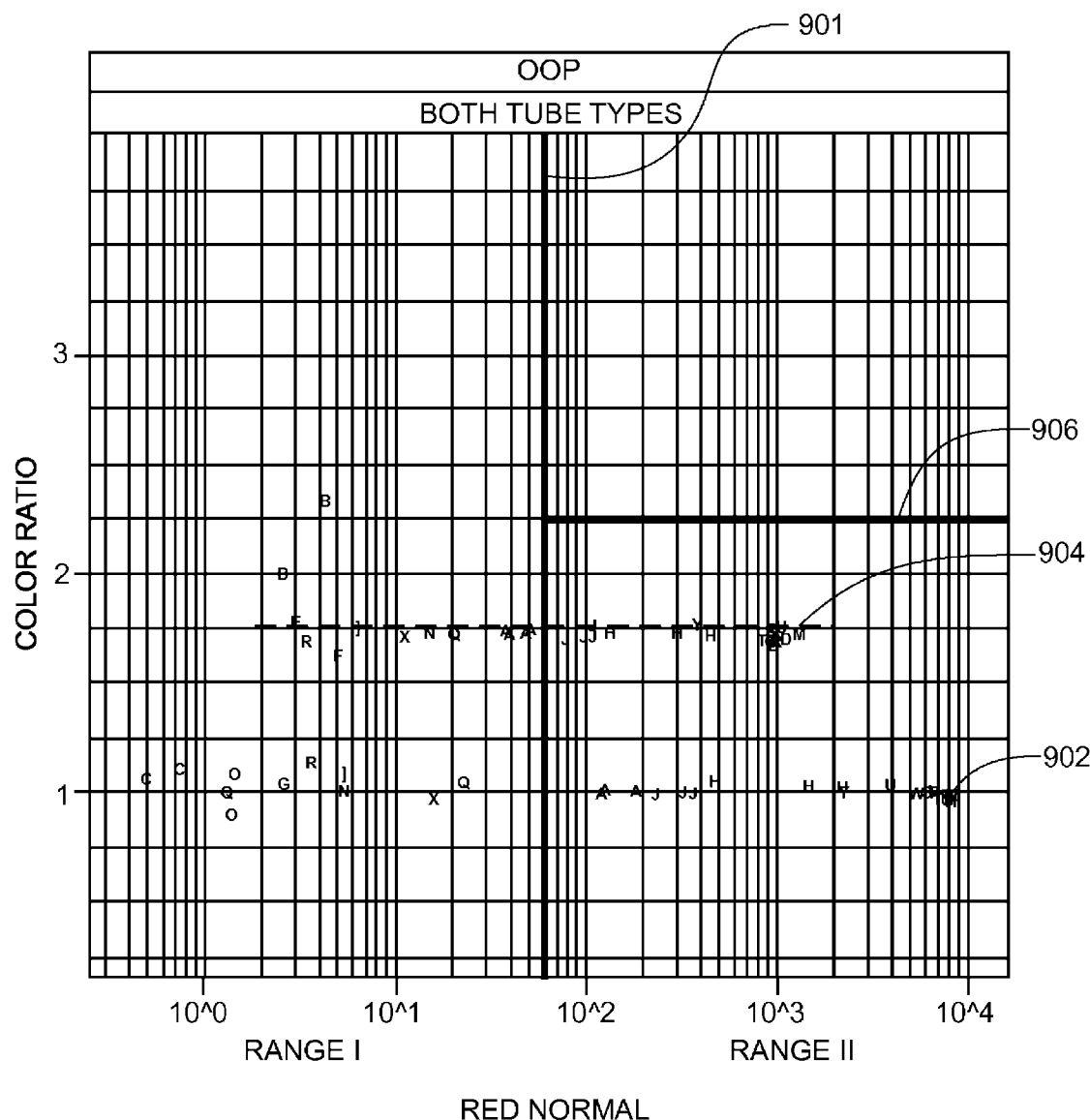

FIGS. 8A and 8B show example experimental test data illustrating the distribution of color ratio v. normalized detector output. FIG. 8A is a graph showing example test data that may be used to empirically determine the color ratio out-of-product thresholds or ranges to be used by controller 258 during out-of-product detection calculations, and specifically during the second comparison (764) of methods such as that of FIG. 7. The graph of FIG. 8A plots the normalized signal output of one of the color ranges (or channels) of detector 252 (e.g., a red detector or a blue detector, for example) when product is present (the baseline) on the x-axis and the color ratio of two or more detectors (e.g., a red detector and a blue detector as in the red-blue color ratio ColorRatio described above) when product is present. In comparison, FIG. 8B plots the same values along the same axes as FIG. 8A, however, the color ratio (y-axis) values are representative of sensor readings when product is absent from the fluid delivery medium. In both plots, the x-axis is shown using a logarithmic scale and the y-axis is shown using a linear scale.

As can be seen from a comparison of FIGS. 8A and 8B, the color ratio exhibits substantially more scattered readings when there is product within the tube than when product is absent. For example, with reference to FIG. 8B, when product is absent from the fluid delivery medium many of the data points lie along a horizontal line 902 at approximately y=1, i.e., indicating current red detector output approximately equal to current blue detector output. This grouping of data points can be associated with products tested in a first type of tubing, e.g., EVA tubing. A second grouping of data points is located along reference line 904 at approximately y=1.75. This grouping of data points can be associated with products tested in a second type of tubing, e.g., Polyflow tubing.

In contrast, the graph of FIG. 8A indicates that when product is present in the line, the color ratio outputs were widely scattered. Data points for both tubing types with product in the line ranged from y<0.5 to y>3.75. Accordingly, the scattering effect exhibited by many color ratio values when product is present can be used to determine color ratio out-of-product thresholds for the sensor. Indeed, the particular color detector outputs selected to comprise the color ratio should be selected to exhibit a larger scattering when product is present relative to scattering when product is absent. This can allow for the setting of out-of-product thresholds that minimize the occurrence of false positives.

FIGS. 8A and 8B further illustrate an example division of the x-axis into two ranges, Range I and Range II. Boundary 901 of these ranges may be determined empirically using the data points to correspond to the majority of color ratio out-of-product events detected for a variety of products having different color, transparency, turbidity, and/or expected batch-to-batch variation, as well as for different types of tubing, such as transparent or translucent. For example, the graphs of FIGS. 8A and 8B include data points for a plurality of products in two types of tubing: Polyflow and EVA.

One or more ranges in FIGS. 8A and 8B can be associated with at least one out-of-product threshold. For example Range I is not associated with an out-of-product threshold. In this example, when the normalized red detector output is such that the product falls within Range I, there is no threshold to satisfy. Accordingly, with reference to the process 750 of FIG. 7, any out-of-product threshold satisfied during the initial comparison (760) will trigger an out-of-product event as no color ratio out-of-product threshold will be satisfied in the subsequent color ratio comparison step (766).

Range II is associated with one color ratio out-of-product threshold 906. In this example, when the normalized red detector output is such that the product falls within Range II and the color ratio is greater than color ratio out-of-product threshold 906 the color ratio out-of-product threshold is deemed to be "satisfied," and no out-of-product event will be triggered. For example, in the process 750 of FIG. 7 any of the color ratios in group 910 which satisfy the color ratio out-of-product threshold 906 would not trigger an out-of-product event even though a detector or combination output of the sensor had satisfied an associated out-of-product threshold. Conversely, a color ratio value within Range II that does not satisfy the color ratio out-of-product threshold 906, would result in a finding of absence of product and trigger an out-of-product event. This additional level of comparison increases the system robustness and can avoid a substantial number of false positives (i.e. all cases where a detector or combination output threshold was satisfied, and the color ratio satisfies an associated color ratio out-of-product threshold).

It should be noted that the color-ratio out-of-product threshold 906 has been selected such that none of the experimental color ratios determined when product was absent (i.e., those in FIG. 8B) satisfy the selected color ratio out-of-product threshold 906. In some embodiments, for example sensors intended for a particular application or where a limited number of products will be included, different product thresholds may be set. For example, if an application is known to use only product and tubing combinations that result in color ratio output along line 902 when product is absent (i.e. in the graph of FIG. 8A), a color ratio out-of-product threshold may be set in both Range I and II that would be satisfied by data points at or above reference line 904.

Sensor 200 may be programmed with the out-of-product thresholds associated with each detector. The out-of-product thresholds for each detector color range, for each combination output, and for each color ratio may be stored in memory 254.

FIG. 6C shows a graph of ratio outputs for a red detector (indicated by triangular data points) a blue detector (indicated by square data points) and a combination output (indicated by circular data points) for three different products. Each product corresponds to one of the areas 830, 832 and 834. FIG. 6C illustrates examples in which only one of the out-of-product threshold tests would satisfy an out-of-product threshold. For example, absence of product A (indicated by area 830) gives only small variations in both the red and blue channels and an out-of-product event would not be detected. However, the combination output would satisfy the out-of-product threshold in this example.

Absence of product B (indicated by area 832) gives small variations in both the red and the combination output that do not satisfy the out-of-product threshold 820. However, the blue detector output does satisfy the out-of-product threshold in this example.

Absence of product C (indicated by area 834) gives small variations in both the combination and the blue detector output that do not satisfy the out-of-product threshold 820. However, the red detector output does satisfy the out-of-product threshold in this example.

Three separate channels, such as the red channel, the blue channel and the combination output, which in this example is the product of the red detector output and the blue detector output, can be evaluated against four thresholds in three ranges each. Two-sided out-of-product thresholds may increase reliability of sensor 200. Sensor 200 according to some embodiments of the present invention works without any preliminary adjustment for different products with very wide variety of optical properties. The same sensor without recalibration can be used in multiple applications. After measuring base line parameters sensor 200 can automatically define ranges and appropriate thresholds from memory and begins monitoring of optical signals to detect an out-of-product events. The combination detector output Xs increases sensitivity for transparent colored products, which, in some cases, cannot be detected using a single channel because they produce small variation in individual output for different color channels. As one example, for some products individual outputs for both red and blue detectors fall in a zone between 0.7 and 0.8 and can not be detected if the threshold is set from 0.6 to 0.65. However, using a calculated combination output Xs may produce an output below the threshold limit and absence of product can be detected.

Thus, embodiments of an optical product detection sensor and methods are disclosed. Although the present invention has been described in considerable detail with reference to certain disclosed embodiments, the disclosed embodiments are presented for purposes of illustration and not limitation and other embodiments of the invention are possible. One skilled in the art will appreciate that various changes, adaptations, and modifications may be made without departing from the spirit of the invention and the scope of the appended claims.

The invention claimed is:

1. A method comprising:
    directing light into a fluid delivery medium in which presence or absence of a product is to be determined;
    detecting light in each of a plurality of wavelength ranges transmitted through the fluid delivery medium and producing therefrom a plurality of detector outputs;
    calculating at least one color ratio based on at least two of the detector outputs;
    normalizing each of the plurality of detector outputs based on baseline detector outputs obtained when product is present in the fluid delivery medium, thereby producing a plurality of normalized detector outputs;
    associating at least one out-of-product threshold with each of the plurality of normalized detector outputs;
    associating at least one color ratio out-of-product threshold with the at least one color ratio;
    performing an initial comparison, wherein each of the normalized detector outputs are compared with the associated at least one out-of-product threshold;
    based on the initial comparison,
        i) determining the presence of product within the fluid delivery medium, or
        ii) triggering a second comparison, wherein each of the at least one color ratios are compared with the associated at least one color ratio out-of-product threshold, the second comparison indicating whether product is present or absent within the fluid delivery medium.

2. The method of claim 1, further comprising:
    calculating at least one combination output based on at least two of the normalized detector outputs; and
    associating the at least one combination output with at least one out-of-product threshold,
    wherein the initial comparison further comprises comparing each of the combination outputs with the associated at least one out-of-product threshold.

3. The method of claim 1, wherein directing light into the fluid delivery medium comprises directing visible light into the fluid delivery medium.

4. The method of claim 1, wherein detecting light in each of a plurality of wavelength ranges comprises detecting light in each of a plurality of distinct wavelength ranges.

5. The method of claim 1, wherein detecting light in each of a plurality of wavelength ranges transmitted through the fluid delivery medium and producing therefrom a plurality of detector outputs comprises detecting light in a red wavelength range and a blue wavelength range and producing therefrom a red detector output and a blue detector output.

6. The method of claim 1, further comprising generating an out-of-product alert upon determination of absence of product in the fluid delivery medium.

7. The method of claim 6, wherein generating an out-of-product alert comprises generating at least one of an audible alert, a visual alert, an e-mail, a page or a text message.

8. The method of claim 1, further comprising correcting each of the plurality of detector outputs for effects of ambient light based on ambient detector outputs obtained when no light is directed into the fluid delivery medium.

9. The method of claim 3, wherein calculating at least one combination output comprises calculating at least one of a sum, a difference, a product or a dividend of at least two of the plurality of detector outputs.

10. The method of claim 1, wherein associating at least one out-of-product threshold with each of the plurality of normalized detector outputs comprises:
    dividing potential detector outputs into a first range, a second range, and a third range; and
    associating at least one out-of-product threshold with each of the first, second and third ranges.

11. The method of claim 10, wherein associating at least one out-of-product threshold with each of the first, second and third ranges comprises associating one out-of-product threshold with the first range, associating two out-of-product thresholds with the second range, and associating one out-of-product threshold with the third range.

12. The method of claim 1, wherein associating the at least one color ratio out-of-product threshold with each color ratio comprises:
    dividing potential detector output of one of the normalized detector outputs into a first range and a second range; and
    associating a color ratio out-of-product threshold with the second range.

13. The method of claim 1, further comprising empirically determining each of the at least one out-of-product thresholds associated with each of the plurality of normalized detector outputs.

14. A sensor, comprising:
    an emitter that directs light into a fluid delivery medium in which presence or absence of a product is to be determined;
    a first detector that generates a first detector output based on detection of light within a first wavelength range transmitted through the fluid delivery medium;
    a second detector that generates a second detector output based on detection of light within a second wavelength range transmitted through the fluid delivery medium;
    a controller that calculates a combination output based on the first and second detector outputs, calculates a color ratio, and determines presence or absence of the product within the fluid delivery medium based on a comparison of the first detector output with at least one first out-of-product threshold, a comparison of the second detector output with at least one second out-of-product threshold, a comparison of the combination output with at least one combined out-of-product threshold, and a comparison of the color ratio with a color ratio out-of-product threshold.

15. The sensor of claim 14, wherein the emitter comprises a white LED.

16. The sensor of claim 14, wherein the first detector comprises a blue photodetector that detects transmitted light within a blue wavelength range and the second detector comprises a red photodetector that detects transmitted light within a red wavelength range.

17. The sensor of claim 14, wherein the controller further generates an out-of-product alert when absence of product within the fluid delivery medium is determined.

18. The sensor of claim 14, wherein the fluid delivery medium comprises one of transparent tubing, translucent tubing or braided tubing.

19. The sensor of claim 14, wherein the product is at least one of a colored product, a transparent product or a turbid product.

20. The sensor of claim 14, wherein the controller further divides each of the first detector output, second detector output, the combination output, and the color ratio into a plurality of ranges and associates one or more of the plurality of ranges with one or more out-of-product thresholds.

21. The sensor of claim 20, wherein the controller determines absence of product within the fluid delivery medium when: a) at least one of the plurality of out-of-product thresholds within at least one of the ranges of the first detector output, the second detector output, or the combination output is satisfied, and b) each of the out-of-product thresholds within each of the ranges of the color ratio are not satisfied.

22. A method comprising:
   directing light into a fluid delivery medium in which presence or absence of a product is to be determined;
   generating a first detector output based on detected light within a first wavelength range transmitted through the fluid delivery medium;
   generating a second detector output based on to detected light within a second wavelength range transmitted through the fluid delivery medium;
   normalizing the first and second detector outputs based on baseline detector outputs obtained when product is present in the fluid delivery medium, thereby producing normalized first and second detector outputs;
   calculating a first combination output based on the normalized first and second detector outputs;
   calculating a second combination output based on the normalized first and second detector outputs;
   calculating a color ratio based on the first and second detector outputs;
   comparing the normalized first detector output with a first group of out-of-product thresholds;
   comparing the normalized second detector output with a second group of out-of-product thresholds;
   comparing the first combination output with a third group of out-of-product thresholds;
   comparing the second combination output with a fourth group of out-of-product thresholds;
   determining presence of product in the fluid delivery medium when none of the out-of-product thresholds of the first, second, third, and fourth groups of out-of-product thresholds are satisfied;
   if any of the out-of-product thresholds of the first, second, third, or fourth groups of out-of-product thresholds are satisfied, comparing the color ratio with a fifth group of out-of-product thresholds; and
   determining absence of product in the fluid delivery medium when none of the out-of-product thresholds of the fifth group of out-of-product thresholds are satisfied.

23. The method of claim 22, wherein normalizing the first detector output comprises calculating a ratio based on the equation:

$$\text{RatioRed} = (Uc\text{Red} - Ud\text{Red})/(Un\text{Red} - Und\text{Red}); \text{ and}$$

wherein normalizing the second detector output comprises calculating a ratio based on the equation:

$$\text{RatioBlue} = (Uc\text{Blue} - Ud\text{Blue})/(Un\text{Blue} - Und\text{Blue});$$

wherein Uc is the current detector output (emitter on); Ud is the current detector output (emitter off); Un is the baseline detector output when fluid is present (emitter on); and Und is the baseline detector output when fluid is present (emitter off).

24. The method of claim 23, wherein the current detector outputs and baseline detector outputs comprise scaled detector outputs according to the following:

$$Ux\text{Red} = (\text{Red Detector Absolute Output}) * (\text{Red Scale Coefficient});$$

$$Ux\text{Blue} = (\text{Blue Detector Absolute Output}) * (\text{Blue Scale Coefficient});$$

wherein UxRed is the scaled detector output for the red sensor; Red Detector Absolute Output is an absolute sensor output value from the red sensor; Red Scale Coefficient is a predetermined coefficient associated with the red detector; UxBlue is the scaled detector output for the blue sensor; Blue Detector Absolute Output is an absolute sensor output value from the blue sensor; and Blue Scale Coefficient is a predetermined coefficient associated with the blue detector.

25. The method of claim 22, wherein the first combination output comprises a product of the normalized first and second detector outputs and the second combination output comprises a ratio of the normalized first and second detector outputs.

* * * * *